United States Patent
Tsuji et al.

(10) Patent No.: US 11,932,600 B2
(45) Date of Patent: Mar. 19, 2024

(54) BIARYL DERIVATIVE

(71) Applicants: DAIICHI SANKYO COMPANY, LIMITED, Tokyo (JP); SANFORD BURNHAM PREBYS MEDICAL DISCOVERY INSTITUTE, La Jolla, CA (US)

(72) Inventors: Takashi Tsuji, Tokyo (JP); Yasunobu Kurosaki, Tokyo (JP); Koutaro Ishibashi, Tokyo (JP); Anthony B. Pinkerton, La Jolla, CA (US)

(73) Assignees: Daiichi Sankyo Company Limited, Tokyo (JP); Sanford Burnham Prebys Medical Discovery Institute, La Jolla, CA (US)

( * ) Notice: Subject to any disclaimer, the term of this patent is extended or adjusted under 35 U.S.C. 154(b) by 410 days.

(21) Appl. No.: 17/287,445

(22) PCT Filed: Oct. 22, 2019

(86) PCT No.: PCT/US2019/057314
§ 371 (c)(1),
(2) Date: Apr. 21, 2021

(87) PCT Pub. No.: WO2020/086504
PCT Pub. Date: Apr. 30, 2020

(65) Prior Publication Data
US 2021/0355087 A1 Nov. 18, 2021

Related U.S. Application Data

(60) Provisional application No. 62/749,590, filed on Oct. 23, 2018.

(51) Int. Cl.
| | | |
|---|---|---|
| C07D 213/71 | (2006.01) |
| A61P 3/14 | (2006.01) |
| C07D 239/38 | (2006.01) |
| C07D 401/12 | (2006.01) |

(52) U.S. Cl.
CPC ............. *C07D 213/71* (2013.01); *A61P 3/14* (2018.01); *C07D 239/38* (2013.01); *C07D 401/12* (2013.01)

(58) Field of Classification Search
CPC .................................................. C07D 213/71
See application file for complete search history.

(56) References Cited

FOREIGN PATENT DOCUMENTS

| | | | |
|---|---|---|---|
| CN | 104334527 A | | 2/2015 |
| CN | 108484584 A | * | 9/2018 |
| WO | 2009017863 A2 | | 2/2009 |
| WO | 2012177668 A1 | | 12/2012 |
| WO | 2013126608 A1 | | 8/2013 |
| WO | 2015084842 A1 | | 6/2015 |
| WO | 2017/007943 A1 | | 1/2017 |

OTHER PUBLICATIONS

A machine generated English translation of CN 108484584 A, Sep. 2018. (Year: 2018).*
Jono, S., et al., "Vascular calcification in chronic kidney disease", J Bone Miner Metab, 24:176-181, 2006.
Weber, C., et al., "Cardiovascular risk markers associated with arterial calcification in patients with chronic kidney disease Stages 3 and 4", Clin. Kidney J., 7:167-173, 2014.
Lanzer, P., et al., "Medial vascular calcification revisited: review and perspectives", European Heart Journal, 35:1515-1525, 2014.
Ossareh, S., "Clinical and economic aspects of sevelamer therapy in end-stage renal disease patients", International Journal of Nephrology and Renovascular Disease, 7:161-168, 2014.
Miao, D., et al., "Histochemical Localization of Alkaline Phosphatase Activity in Decalcified Bone and Cartilage", The Journal of Histochemistry & Cytochemistry, 50(3):333-340, 2002.
Lomashvili, et al., "Phosphate-Induced Vascular Calcification: Role of Pyrophosphate and Osteopontin", J Am Soc Nephrol, 15:1392-1401, 2004.
Narisawa, S., et al., "In Vivo Overexpression of Tissue-Nonspecific Alkaline Phosphatase Increases Skeletal Mineralization and Affects the Phosphorylation Status of Osteopontin", J Bone Miner Res, 28(7):1587-1598, 2013.

(Continued)

*Primary Examiner* — Laura L Stockton
(74) *Attorney, Agent, or Firm* — Christensen O'Connor Johnson Kindness PLLC

(57) ABSTRACT

The present invention relates to a compound or a pharmacologically acceptable salt thereof having excellent tissue non-specific alkaline phosphatase inhibitory activity. The present invention provides a compound represented by the following formula (I): wherein $X^1$ represents a nitrogen atom or $CR^9$, $R^1$ represents a hydrogen atom, a $C^1$-$C^6$ alkyl group, or a $C^1$-$C^6$ alkoxy group, $R^2$ represents a halogen atom, $R^3$ represents a hydrogen atom or a halogen atom, $R^4$ represents a hydrogen atom or a halogen atom, and $R^5$ represents a $C^1$-$C^3$ alkylsulfonyl group, a substituted $C^1$-$C^6$ alkyl group, a substituted $C^1$-$C^6$ haloalkyl group, a substituted $C^1$-$C^6$ alkoxy group, or a substituted $C^1$-$C^6$ alkylamino group, or a pharmacologically acceptable salt thereof.

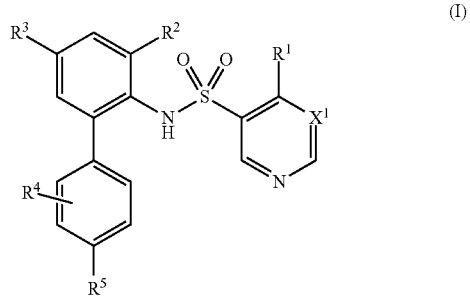

(I)

16 Claims, No Drawings

(56) References Cited

OTHER PUBLICATIONS

Narisawa, S., et al., "Novel Inhibitors of Alkaline Phosphatase Suppress Vascular Smooth Muscle Cell Calcification", Journal of Bone and Mineral Research, 22(11):1700-1710, 2007.
Sidique, S., et al., "Design and synthesis of pyrazole derivatives as potent and selective inhibitors of tissue- nonspecific alkaline phosphatase (TNAP)", Bioorganic & Medicinal Chemistry Letters, 19:222-225, 2009.
Debray, J., et.al., "Inhibitors of tissue-nonspecific alkaline phosphatase: Design, synthesis, kinetics, biomineralization and cellular tests", Bioorganic & Medicinal Chemistry, 21:7981-7987, 2013.
Dahl, R., et al., "Discovery and Validation of a Series of Aryl Sulfonamides as Selective Inhibitors of Tissue-Nonspecific Alkaline Phosphatase (TNAP)", J. Med. Chem, XP002669256, 52:6919-6925, 2009.
Chung, T., et al., "Assay Format as a Critical Success Factor for Identification of Novel Inhibitor Chemotypes of Tissue-Nonspecific Alkaline Phosphatase from High-Throughput Screening", Molecules, XP055652155, 15:3010-3037, 2010.
International Search Report dated Jan. 3, 2020, issued in corresponding International Application No. PCT/US2019/057314, filed Oct. 22, 2019, 2 pages.
Written Opinion Of the International Searching Authority dated Jan. 3, 2020, issued in corresponding International Application No. PCT/US2019/057314, filed Oct. 22, 2019, 5 pages.

\* cited by examiner

BIARYL DERIVATIVE

CROSS-REFERENCE TO RELATED APPLICATIONS

This application is a US national stage application based on PCT/US2019/057314, filed Oct. 22, 2019, which claims the benefit of U.S. Application No. 62/749,590, filed Oct. 23, 2018, each expressly incorporated herein by reference in its entirety.

BACKGROUND OF THE INVENTION

Field of the Invention

The present invention relates to a novel biaryl derivative or a pharmacologically acceptable salt thereof which has excellent tissue non-specific alkaline phosphatase (hereinafter, referred to as TNAP) inhibitory activity.

The present invention also relates to a therapeutic agent and/or prophylactic agent (preferably a therapeutic agent) for pseudoxanthoma elasticum (PXE), generalized arterial calcification of infancy (GACI), craniometaphyseal dysplasia (CMD), ossification of the yellow ligament (OYL), arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL), ossification of the anterior longitudinal ligament (OALL), diffuse idiopathic skeletal hyperostosis (DISH), meniscal calcification, or peritoneal calcification, comprising the compound or the pharmacologically acceptable salt thereof as an active ingredient.

The present invention further relates to a composition for the prophylaxis or treatment of the aforementioned diseases, comprising the compound of formula (I) or the pharmacologically acceptable salt thereof as an active ingredient, use of the compound of formula (I) or the pharmacologically acceptable salt thereof for manufacturing a pharmaceutical for the prophylaxis or treatment of the disease, and a method for the prophylaxis or treatment of the disease, comprising administering a pharmacologically effective amount of the compound of formula (I) or the pharmacologically acceptable salt thereof to a mammal (preferably a human).

Description of the Related Art

In vivo calcification is strictly regulated by the balance of activation between osteoblasts and osteoclasts, phosphorus and calcium concentrations in plasma, and parathyroid hormone or vitamin D secreted in order to maintain the homeostasis of these concentrations (Non Patent Literature 1). Ectopic calcification is found in diseases, for example, pseudoxanthoma elasticum (PXE), generalized arterial calcification of infancy (GACI), craniometaphyseal dysplasia (CMD), ossification of the yellow ligament (OYL), arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL), ossification of the anterior longitudinal ligament (OALL), diffuse idiopathic skeletal hyperostosis (DISH), meniscal calcification, and peritoneal calcification. In these pathological conditions, calcification in tissues (blood vessels, soft tissues, etc.) that are usually not calcified is caused by the failure of the regulatory mechanism mentioned above, and is known to bring about significantly reduced quality of life (QOL) due to the limitation of activity and an increased cardiovascular risk (Non Patent Literatures 2 and 3). No existing therapeutic agent is effective for ectopic calcification. Thus, there are very high unmet medical needs for this disease (Non Patent Literature 4).

TNAP, one of alkaline phosphatases, includes membrane-bound and secretory forms. TNAP is expressed in the bone, the liver, and the kidney and highly expressed particularly in the matrix vesicles of chondrocytes and osteoblasts. This enzyme is known to play an important role in in vivo calcification via the degradation of pyrophosphate, which is an endogenous anti-calcification factor (Non Patent Literature 5). A large number of reports show the increased expression level or elevated activity of TNAP at lesion sites of ectopic calcification, and ectopic calcification also occurs in mice which overexpress human TNAP, suggesting the importance of TNAP for ectopic calcification (Non Patent Literatures 6 and 7). Thus, the inhibition of TNAP is considered to elevate pyrophosphate concentrations in blood and in tissues and suppress ectopic calcification (Non Patent Literature 8).

Some compounds are known to have TNAP inhibitory activity (see e.g., Patent Literatures 1 and 2 and Non Patent Literatures 9 to 11). Nonetheless, a biaryl compound having a substituent at the 3-position has not yet been disclosed.

Furthermore, disclosed compounds partially having a common skeleton differ from the compound of the present invention in purpose (Patent Literatures 3 and 4).

CITATION LIST

Patent Literature

[Patent Literature 1] International Publication No. WO 2009/017863 (PCT/US2008/063106)

[Patent Literature 2] International Publication No. WO 2013/126608 (U.S. Patent Publication No. 2015-0011551)
[Patent Literature 3] International Publication No. WO 2012/177668
[Patent Literature 4] International Publication No. WO 2015/084842

Non Patent Literature

[Non Patent Literature 1] J. Bone Miner Res, 2006, vol. 24, p. 176-181
[Non Patent Literature 2] Clin. Kidney J., 2014, vol. 7, p. 167-173
[Non Patent Literature 3] Eur. Heart. J., 2014, vol. 35, p. 1515-1525
[Non Patent Literature 4] Int. J. Nephrol. Renovasc. Dis., 2014, vol. 7, p. 161-168
[Non Patent Literature 5] J. Histochem. Cytochem., 2002, vol. 50, p. 333-340
[Non Patent Literature 6] J. Am. Soc. Nephrol., 2004, vol. 15, p. 1392-1401
[Non Patent Literature 7] J. Bone Miner Res, 2013, vol. 7, p. 1587-1598
[Non Patent Literature 8] J. Bone Miner Res, 2007, vol. 22, p. 1700-1710
[Non Patent Literature 9] Bioorg. Med. Chem. Lett., 2009, vol. 19, p. 222-225
[Non Patent Literature 10] J. Med. Chem, 2009, vol. 52, p. 6919-6925
[Non Patent Literature 11] Bioorg. Med. Chem., 2013, vol. 21, p. 7981-7987

SUMMARY OF THE INVENTION

The present inventors have conducted diligent studies and consequently found that a compound represented by the formula (I) has excellent TNAP inhibitory activity based on its specific chemical structure, further has excellent properties in terms of the physicochemical properties (e.g., stability) of a pharmaceutical, and serves as a safe and useful pharmaceutical as a prophylactic or therapeutic agent for a pathological condition or a disease associated with ectopic calcification. On the basis of these findings, the present invention has been completed.

Specifically, the compound of the present invention has excellent properties in terms of TNAP inhibitory activity, solubility, cell membrane permeability, oral absorbability, concentration in blood, metabolic stability, tissue penetration, bioavailability (hereinafter, also referred to as BA), in vitro activity, in vivo activity, ex vivo activity, quick onset of drug efficacy, persistence of drug efficacy, physical stability, drug interaction, safety (e.g., cardiotoxicity or hepatotoxicity), and is useful as a pharmaceutical [particularly, a pharmaceutical for the treatment or prophylaxis (preferably treatment) of pseudoxanthoma elasticum (PXE), generalized arterial calcification of infancy (GACI), craniometaphyseal dysplasia (CMD), ossification of the yellow ligament (OYL), arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL), ossification of the anterior longitudinal ligament (OALL), diffuse idiopathic skeletal hyperostosis (DISH), meniscal calcification, or peritoneal calcification].

More Specifically, the Present Invention is as Described Below

[1]

A compound represented by formula (I):

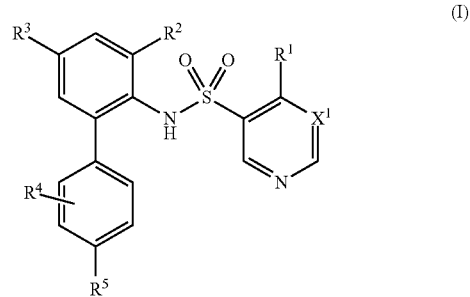

wherein $X^1$ represents a nitrogen atom or $CR^9$, $R^1$ represents a hydrogen atom, a C1-C6 alkyl group or a C1-C6 alkoxy group, $R^2$ represents a halogen atom, $R^3$ represents a hydrogen atom or a halogen atom, $R^4$ represents a hydrogen atom or a halogen atom, $R^5$ represents a C1-C3 alkylsulfonyl group, a C1-C6 alkyl group (wherein the alkyl group is substituted by one group selected from a C1-C3 alkylsulfonyl group, a carboxy group and a tetrazolyl group), a C1-C6 haloalkyl group (wherein the haloalkyl group is substituted by one group selected from a C1-C3 alkylsulfonyl group, a carboxy group and a tetrazolyl group), a C1-C6 alkoxy group (wherein the alkoxy group is substituted by one group selected from a C1-C3 alkylsulfonyl group, a carboxy group and a tetrazolyl group) or a C1-C6 alkylamino group (wherein the alkylamino group is substituted by one group selected from a C1-C3 alkylsulfonyl group, a carboxy group and a tetrazolyl group), and $R^9$ represents a hydrogen atom, a halogen atom, a C1-C3 alkylsulfonyl group, a C1-C6 alkyl group or a C1-C6 alkoxy group, or a pharmacologically acceptable salt thereof.

[2]
A compound represented by formula (II):

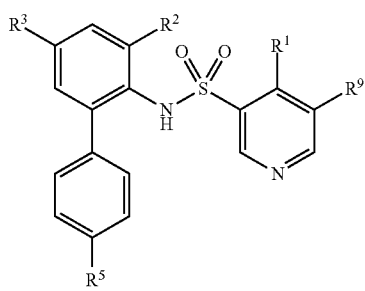
(II)

wherein

R¹ represents a hydrogen atom or a C1-C3 alkyl group,

R² represents a halogen atom,

R³ represents a halogen atom,

R⁵ represents a C1-C6 alkyl group (wherein the alkyl group is substituted by one group selected from a C1-C3 alkylsulfonyl group, a carboxy group and a tetrazolyl group), a C1-C6 alkoxy group (wherein the alkoxy group is substituted by one group selected from a C1-C3 alkylsulfonyl group, a carboxy group and a tetrazolyl group) or a C1-C6 alkylamino group (wherein the alkylamino group is substituted by one group selected from a C1-C3 alkylsulfonyl group, a carboxy group and a tetrazolyl group), and R⁹ represents a C1-C3 alkyl group or a C1-C3 alkoxy group, or a pharmacologically acceptable salt thereof.

[3]
A compound represented by formula (III):

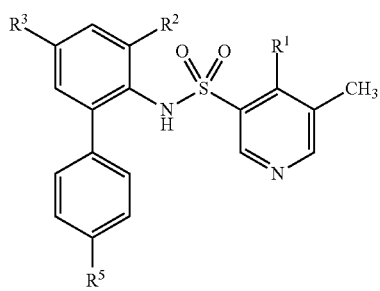
(III)

wherein

R¹ represents a hydrogen atom, a methyl group or an ethyl group,

R² represents a fluorine atom or a chlorine atom,

R³ represents a halogen atom, and

R⁵ represents a C1-C6 alkyl group substituted by one carboxy group or a C1-C6 alkoxy group substituted by one carboxy group, or a pharmacologically acceptable salt thereof.

[4]
A compound represented by

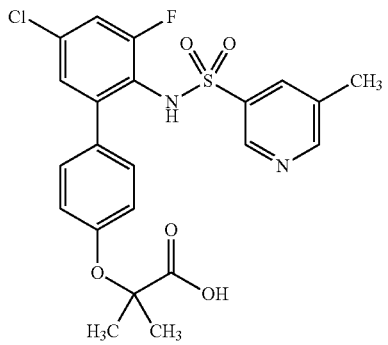 [SMILES: Cc1cncc(S(=O)(=O)Nc2c(F)cc(Cl)cc2-c2ccc(OC(C)(C)C(=O)O)cc2)c1]

or a pharmacologically acceptable salt thereof.

[5]
A compound represented by

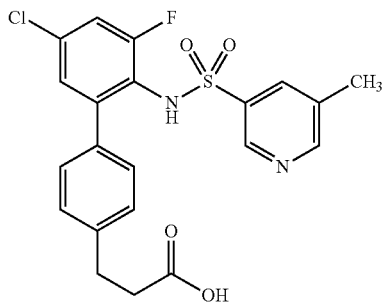 [SMILES: Cc1cncc(S(=O)(=O)Nc2c(F)cc(Cl)cc2-c2ccc(CCC(=O)O)cc2)c1]

or a pharmacologically acceptable salt thereof.

[6]
A compound represented by

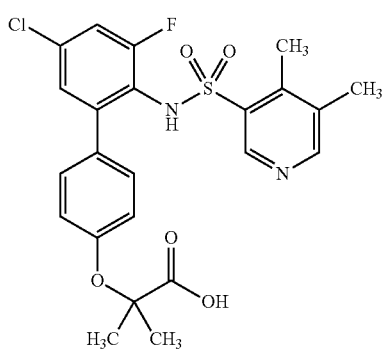 [SMILES: Cc1cncc(S(=O)(=O)Nc2c(F)cc(Cl)cc2-c2ccc(OC(C)(C)C(=O)O)cc2)c1C]

or a pharmacologically acceptable salt thereof.

[7]
A compound represented by

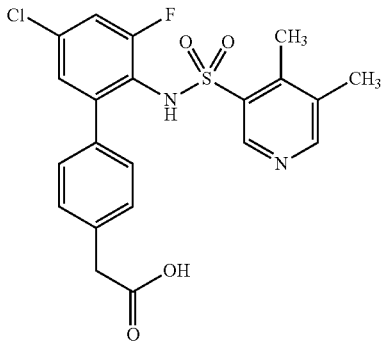 [SMILES: Cc1cncc(S(=O)(=O)Nc2c(F)cc(Cl)cc2-c2ccc(CC(=O)O)cc2)c1C]

or a pharmacologically acceptable salt thereof.

[8]
A compound of any one of [1] to [7], wherein the pharmacologically acceptable salt is a sodium salt or a potassium salt.

[9]
A pharmaceutical composition comprising a compound according to any one of [1] to [7] or a pharmacologically acceptable salt thereof, as an active ingredient.

[10]
The pharmaceutical composition according to [9], for the treatment or prophylaxis of ectopic calcification.

[11]
The pharmaceutical composition according to [9], for the treatment or prophylaxis of pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), or aortic stenosis.

[12]
The pharmaceutical composition according to [9], for the treatment or prophylaxis of pseudoxanthoma elasticum (PXE).

[13]
A TNAP inhibitor comprising a compound according to any one of [1] to [7] or a pharmacologically acceptable salt thereof, as an active ingredient.

[14]
A method for inhibiting TNAP in a subject, comprising administering a pharmacologically effective amount of a compound according to any one of [1] to [7] or a pharmacologically acceptable salt thereof to a subject in need thereof.

[15]
A method for the prophylaxis or treatment of ectopic calcification, comprising administering a pharmacologically effective amount of a compound according to any one of [1] to [7] or a pharmacologically acceptable salt thereof to a subject in need thereof.

[16]
A method for the prophylaxis or treatment of a disease or condition selected from the group consisting of pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis, comprising administering a pharmacologically effective amount of a compound according to any one of [1] to [7] or a pharmacologically acceptable salt thereof to a subject in need thereof.

[17]
The method according to [16], wherein the disease or condition is pseudoxanthoma elasticum (PXE).

[18]
The method according to any one of [14] to [17], wherein the subject is a human.

[19]
Use of a compound according to any one of [1] to [7] or a pharmacologically acceptable salt thereof for manufacturing a pharmaceutical composition.

[20]
A compound according to any one of [1] to [7] or a pharmacologically acceptable salt thereof for inhibiting TNAP in a subject.

[21]
A compound according to any one of [1] to [7] or a pharmacologically acceptable salt thereof for use in the treatment of ectopic calcification.

[22]
A compound according to any one of [1] to [7] or a pharmacologically acceptable salt thereof for use in the treatment of a disease or condition selected from the group consisting of pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis.

[23]
A compound according to any one of [1] to [7] or a pharmacologically acceptable salt thereof for use in the treatment of pseudoxanthoma elasticum (PXE).

In the present invention, the "C1-C6 alkyl group" refers to a linear or branched alkyl group having 1 to 6 carbon atoms. Examples thereof can include methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. For $R^9$, $R^1$ or $R^6$, the C1-C6 alkyl group is preferably an alkyl group having 1 to 3 carbon atoms, most preferably an ethyl or methyl group.

In the present invention, the "C1-C3 alkylsulfonyl group" refers to the "C1-C3 alkyl group" bonded to a sulfonyl group. Examples thereof can include methylsulfonyl, ethylsulfonyl, isopropylsulfonyl, and n-propylsulfonyl groups. For $R^5$, the C1-C3 alkylsulfonyl group is preferably a methylsulfonyl or ethylsulfonyl group.

In the present invention, the "C1-C6 alkoxy group" refers to the aforementioned "C1-C6 alkyl group" bonded to an oxygen atom. Examples thereof can include linear or branched alkoxy groups each having 1 to 6 carbon atoms, such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups. For $R^1$, the C1-C6 alkoxy group is preferably a methoxy or ethoxy group.

In the present invention, the "C1-C6 alkylamino group" refers to the aforementioned "C1-C6 alkyl group" bonded to a nitrogen atom. Examples thereof can include methylamino, ethylamino, n-propylamino, isopropylamino, n-butylamino, isobutylamino, s-butylamino, tert-butylamino, n-pentylamino, isopentylamino, 2-methylbutylamino, neopentylamino, 1-ethylpropylamino, n-hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino and 2-ethylbutylamino groups. For $R^5$, the C1-C6 alkylamino group is preferably an alkylamino group having 1 to 3 carbon atoms, most preferably a methylamino, ethylamino or isopropylamino group.

In the present invention, the "C1-C6 haloalkyl group" refers to the aforementioned "C1-C6 alkyl group" substituted by 1 or 2 or more halogen atoms. Examples thereof can include fluoromethyl, difluoromethyl, chloromethyl, dichloromethyl, chlorofluoromethyl, 1,1-difluoroethyl, 1,1-dichloroethyl, 1,1,2,2-tetrafluoroethyl, 1,1-difluoropropyl, 1,1-difluorobutyl, 2,2-difluoropropyl, 1,1-difluoropentyl, 1-fluoro-2,2-dimethylpropyl, 1,1-difluoro-2,2-dimethylpropyl and 1,1-difluoro-2,2-dimethylbutyl groups. For $R^5$, the C1-C6 haloalkyl group is preferably a haloalkyl group having 1 to 3 carbon atoms, most preferably a difluoromethyl, 1,1-difluoroethyl or dichloromethyl group.

In the present invention, the "C1-C6 alkylene group" refers to a linear or branched alkylene group having 1 to 6 carbon atoms. Examples thereof can include methylene, ethylene, n-propylene, n-butylene, propane-2,2-diyl, propane-2,3-diyl, butyl-2,3-diyl, butyl-2,4-diyl, n-pentylene, 2-methylbutyl-2,4-diyl, pentyl-2,4-diyl, pentyl-2,5-diyl, n-hexylene and 2-methylpropyl-2,5-diyl groups. For $X^2$, the C1-C6 alkylene group is preferably a methylene group or an ethylene group.

In the present invention, the "C1-C6 haloalkylene group" refers to the aforementioned "C1-C6 alkylene group" substituted by a halogen atom. Examples thereof can include fluoromethylene, difluoromethylene, chloromethylene, dichloromethylene, chlorofluoromethylene, 1,1-difluoroethylene, 1,1-dichloroethylene, 1,1,2,2-tetrafluoroethylene, 1,1-difluoropropylene, 1,1-difluorobutylene, 2,2-difluoropropylene, 1-fluoro-2,2-dimethylpropylene, 1,1-difluoro-2,2-dimethylpropylene and 1,1-difluoro-2,2-dimethylbutylene groups. For $X^2$, the C1-C6 haloalkylene group is preferably a difluoromethylene group.

In the present invention, the "C1-C6 alkyleneoxy group" refers to the aforementioned "C1-C6 alkylene group" bonded to an oxygen atom. Examples thereof can include methyleneoxy, ethyleneoxy, n-propyleneoxy, n-butyleneoxy, propane-2-oxy-2-yl, propane-2-oxy-3-yl, butyl-2-oxy-3-yl, butyl-2-oxy-4-yl, n-pentyleneoxy, 2-methylbutyl-2-oxy-4-yl, pentyl-2-oxy-4-yl, pentyl-2-oxy-5-yl, n-hexyleneoxy and 2-methylpropyl-2-oxy-5-yl groups. For $X^2$, the C1-C6 alkyleneoxy group is preferably a methyleneoxy group or a propane-2-oxy-2-yl group.

In the present invention, the "halogen atom" refers to a fluorine atom, a chlorine atom, a bromine atom or an iodine atom. For $R^2$, $R^3$ or $R^4$, the halogen atom is preferably a fluorine atom or a chlorine atom. For $Y^1$, the halogen atom is preferably a bromine atom or an iodine atom.

$R^9$ of the present invention is preferably a methyl group or an ethyl group, more preferably a methyl group.

$R^1$ of the present invention is preferably a hydrogen atom or a C1-C3 alkyl group, more preferably a hydrogen atom, a methyl group or an ethyl group.

Each of $R^2$, $R^3$ and $R^4$ of the present invention is preferably a halogen atom.

$R^5$ of the present invention is preferably a C1-C6 alkyl group optionally substituted by one carboxy group, or a C1-C6 alkoxy group optionally substituted by one carboxy group.

$R^6$ of the present invention is preferably a C1-C6 alkyl group, most preferably an ethyl group or a methyl group.

$R^8$ of the present invention is preferably a C1-C6 alkyl group optionally substituted by one carboxy group.

$R^9$ of the present invention is preferably a methyl group or an ethyl group, more preferably a methyl group.

$X^1$ of the present invention is preferably $CR^9$.

$X^2$ of the present invention is preferably a C1-C6 alkylene group or a C1-C6 alkyleneoxy group.

$Y^1$ of the present invention is preferably a bromine atom or an iodine atom.

$Y^2$ of the present invention is preferably boronic acid or boronic acid ester.

$L^1$ of the present invention is preferably a trityl group or a tetrahydropyranyl group.

$L^2$ of the present invention is preferably a tert-butoxycarbonyl group.

In certain embodiments, the compound represented by the general formula (I) of the present invention can form a salt with a base. Such a salt with a base is included in the scope of the present invention. Examples of the salt with a base can include: alkali metal salts such as lithium salt, sodium salt, potassium salt, and cesium salt; alkaline earth metal salts such as magnesium salt, calcium salt, and barium salt; inorganic nitrogen compound salts such as ammonium salt and hydrazine salt; primary amine salts such as methylamine salt, ethylamine salt, n-propylamine salt, isopropylamine salt, n-butylamine salt, 2-butylamine salt, isobutylamine salt, and tert-butylamine salt; secondary amine salts such as dimethylamine salt, diethylamine salt, diisopropylamine salt, pyrrolidine salt, piperidine salt, and morpholine salt; tertiary amine salts such as triethylamine salt and N-methylmorpholine salt; and aromatic amine salts such as pyridine salt, 4-(N,N-dimethylamino)pyridine salt, imidazole salt, and 1-methylimidazole salt. The salt is preferably an alkali metal salt, most preferably sodium salt or potassium salt. The compound represented by the general formula (I) of the present invention can form any ratio of a salt with a base. The respective salts with bases or mixtures thereof are included in the scope of the present invention.

In certain embodiments, the compound represented by the general formula (I) of the present invention can form an acid-addition salt, depending on its substituent. Such an acid-addition salt is included in the scope of the present invention. The compound represented by the general formula (I) of the present invention can form any ratio of an acid-addition salt, depending on its substituent. The respective acid-addition salts (e.g., monoacid salt and hemi-acid salt) or mixtures thereof are included in the present invention.

The compound represented by the general formula (I) of the present invention or the pharmacologically acceptable salt thereof can form an anhydrate, a hydrate, or a solvate. The respective forms or mixtures thereof are included in the scope of the present invention.

When the compound represented by the general formula (I) of the present invention or the pharmacologically acceptable salt thereof has at least one asymmetric center, carbon-carbon double bond, axial chirality, tautomerism, or the like, optical isomers (including enantiomers and diastereomers), geometric isomers, rotational isomers, and tautomers may exist. These isomers and mixtures thereof are represented by a single formula such as the formula (I). The present invention encompasses these isomers and mixtures (including racemates) thereof at any ratio.

The compound represented by the general formula (I) of the present invention or the pharmacologically acceptable salt thereof can form an isotopic compound by the replacement of one or more atoms constituting the compound or the salt with isotopes at nonnatural ratios. The isotopes can be radioactive or nonradioactive. Examples thereof include deuterium ($^2H$; D), tritium ($^3H$; T), carbon-14 ($^{14}C$), and iodine-125 ($^{125}I$). The radioactive or nonradioactive isotopic compound may be used as a pharmaceutical for the treatment or prophylaxis of a disease, a reagent for research (e.g., a reagent for assay), a diagnostic agent (e.g., a diagnostic imaging agent), or the like. The present invention encompasses these radioactive or nonradioactive isotopic compounds.

The compound represented by the general formula (I) of the present invention can be produced by, for example, methods given below.

Typical methods for the manufacture of the compound represented by the general formula (I) of the present invention will be described.

The solvent for use in the reaction of each step in the manufacture methods given below is not particularly limited as long as the solvent partially dissolves starting materials without inhibiting the reaction. The solvent is selected from, for example, the following solvent group: aliphatic hydrocarbons such as hexane, pentane, heptane, petroleum ether, and cyclohexane; aromatic hydrocarbons such as toluene, benzene, and xylene; halogenated hydrocarbons such as dichloromethane, chloroform, carbon tetrachloride, dichloroethane, chlorobenzene, and dichlorobenzene; ethers such as diethyl ether, diisopropyl ether, cyclopentyl methyl ether, t-butyl methyl ether, tetrahydrofuran, 1,4-dioxane, dimethoxyethane, and diethylene glycol dimethyl ether; ketones such as acetone, methyl ethyl ketone, methyl isobutyl ketone, and cyclohexanone; esters such as methyl acetate, ethyl acetate, propyl acetate, butyl acetate, and diethyl carbonate; nitriles such as acetonitrile, propionitrile, butyronitrile, and isobutyronitrile; organic acids such as formic acid, acetic acid, propionic acid, trifluoroacetic acid, and pentafluoropropionic acid; alcohols such as methanol, ethanol, 1-propanol, 2-propanol, 1-butanol, 2-butanol, 2-methyl-1-propanol, and 2-methyl-2-propanol; amides such as formamide, N,N-dimethylformamide, N,N-dimethylacetamide, N-methylpyrrolidone, N,N'-dimethylpropyleneurea, and hexamethylphosphortriamide; sulfoxides such as dimethyl sulfoxide and sulfolane; water; and mixtures thereof.

The acid for use in the reaction of each step in the manufacture methods given below is not particularly limited as long as the acid does not inhibit the reaction. The acid is selected from the following acid group: inorganic acids such as hydrochloric acid, hydrobromic acid, hydroiodic acid, phosphoric acid, sulfuric acid, and nitric acid; organic acids such as formic acid, acetic acid, propionic acid, trifluoroacetic acid, and pentafluoropropionic acid; and organic sulfonic acids such as methanesulfonic acid, trifluoromethanesulfonic acid, p-toluenesulfonic acid, and camphorsulfonic acid.

The base for use in the reaction of each step in the manufacture methods given below is not particularly limited as long as the base does not inhibit the reaction. The base is selected from the following base group: alkali metal carbonates such as lithium carbonate, sodium carbonate, potassium carbonate, and cesium carbonate; alkali metal bicarbonates such as lithium bicarbonate, sodium bicarbonate, and potassium bicarbonate; alkali metal hydroxides such as lithium hydroxide, sodium hydroxide, and potassium hydroxide;

alkaline earth metal hydroxides such as calcium hydroxide and barium hydroxide; alkali metal phosphates such as sodium phosphate and potassium phosphate; alkali metal hydrides such as lithium hydride, sodium hydride, and potassium hydride; alkali metal amides such as lithium amide, sodium amide, and potassium amide; metal alkoxides such as lithium methoxide, sodium methoxide, sodium ethoxide, sodium tert-butoxide, and potassium tert-butoxide; lithium amides such as lithium diisopropylamide (LDA), lithium cyclohexylisopropylamide, and lithium tetramethylpiperazide; alkali metal silylamides such as lithium bistrimethylsilylamide, sodium bistrimethylsilylamide, and potassium bistrimethylsilylamide; alkyllithiums such as methyllithium, n-butyllithium, sec-butyllithium, and tert-butyllithium; alkyl magnesium halides such as methyl magnesium chloride, methyl magnesium bromide, methyl magnesium iodide, ethyl magnesium chloride, ethyl magnesium bromide, isopropyl magnesium chloride, isopropyl magnesium bromide, and isobutyl magnesium chloride; and organic amines such as triethylamine, tributylamine, diisopropylethylamine, diethylamine, diisopropylamine, N-methylpiperidine, N-methylmorpholine, N-ethylmorpholine, pyridine, picoline, 2,6-lutidine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO), and 1,8-diazabicyclo[5.4.0]-7-undecene (DBU).

In the reaction of each step in the manufacture methods given below, the reaction temperature differs depending on solvents, starting materials, reagents, etc., and the reaction time differs depending on solvents, starting materials, reagents, etc.

After the completion of the reaction of each step in the manufacture methods given below, the compound of interest of each step is isolated from the reaction mixture according to a routine method. The compound of interest is obtained, for example, by: (i) if necessary, filtering off insoluble matter such as a catalyst; (ii) adding water and a water-immiscible solvent (e.g., dichloromethane, chloroform, diethyl ether, ethyl acetate, or toluene) to the reaction mixture to extract the compound of interest; (iii) washing the organic layer with water, followed by drying using a desiccant such as anhydrous sodium sulfate or anhydrous magnesium sulfate; and (iv) distilling off the solvent. The obtained compound of interest can be further purified, if necessary, by a routine method, for example, recrystallization, reprecipitation, or silica gel column chromatography. Alternatively, the compound of interest of each step may be used directly in the next reaction without being purified.

[Manufacture Method 1]

Compound (Ia) represented by the general formula (I) wherein $R^5$ represents a C1-C6 alkyl group substituted by one carboxy group, a C1-C6 haloalkyl group substituted by one carboxy group, or a C1-C6 alkoxy group substituted by one carboxy group can be produced by, for example, the following method:

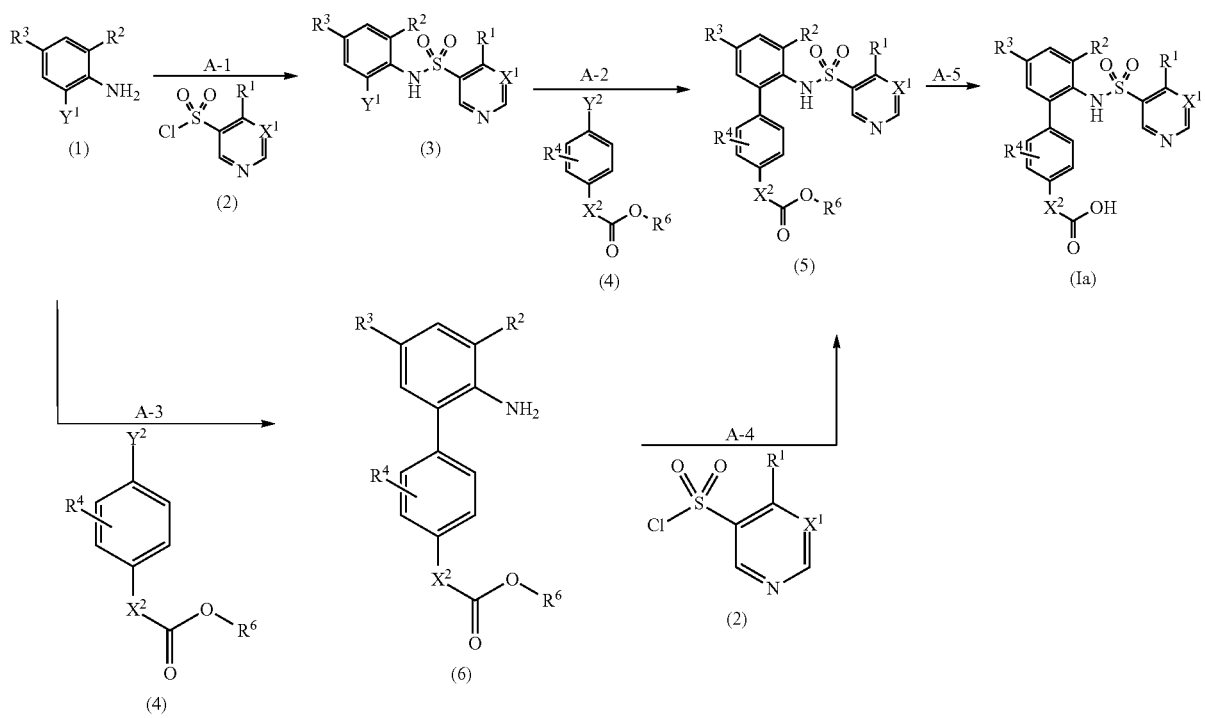

In the structural formulas of the compounds in [manufacture method 1] described above, $R^1$, $R^2$, $R^3$, $R^4$, and $X^1$ are as defined in the general formula (I); $X^2$ represents a C1-C6 alkylene group, a C1-C6 haloalkylene group or a C1-C6 alkyleneoxy group; $R^6$ represents a substituent generally used as a protective group for carboxylic acid, for example, a C1-C6 alkyl group; $Y^1$ represents a substituent necessary for bonding compound (1) to compound (4) and is, for example, a halogen atom or a trifluoromethanesulfonyloxy group; and $Y^2$ represents a substituent necessary for bonding compound (1) to compound (4) and is, for example, a boryl group, a magnesium halide or a zinc halide, preferably a boryl group. The boryl group is a dihydroxyboryl group, a tetrafluoroboryl group, a pinacolboryl group, a neopentyl glycol boryl group, or the like, preferably a dihydroxyboryl group or a pinacolboryl group. The magnesium halide refers to magnesium chloride, magnesium bromide, or the like, and the zinc halide refers to zinc chloride, zinc bromide, or the like.

Step A-1 is the step of reacting compound (1) with compound (2) in the presence of a base to produce compound (3). Each of the compound (1) and the compound (2) is commercially available or can be easily prepared from a compound known in the art.

The base used is an organic amine. The base is preferably triethylamine, diisopropylethylamine or pyridine, more preferably pyridine.

The solvent used is preferably an aromatic hydrocarbon, a halogenated hydrocarbon, an ether, an amide, a sulfoxide, or is absent, more preferably tetrahydrofuran, N,N-dimethylformamide, dimethyl sulfoxide, or is absent, further preferably is absent.

The reaction temperature is preferably room temperature to 80° C.

The reaction time is 1 hour to 24 hours, preferably 12 hours.

Step A-2 is the step of subjecting the compound (3) obtained in the step A-1 to coupling reaction with compound (4) in the presence of a transition metal catalyst to produce compound (5).

The compound (4) refers to any of various organometal compounds for use in coupling with halogenated aryl and is preferably a boronic acid compound or a boronic acid ester compound, more preferably a boronic acid pinacol ester compound. The compound (4) is commercially available or can be easily prepared from a compound known in the art.

This step is not particularly limited as long as the step does not influence the other parts of the compound.

This step can generally be carried out by a method well known in the techniques of organic synthetic chemistry, for example, a method described in Palladium Reagents and Catalysts (2004, John Wiley & Sons Ltd.).

The metal catalyst used may be a palladium metal catalyst generally used in coupling reaction and is preferably tetrakis (triphenylphosphine)palladium, [1,1'-bis(diphenylphosphino)ferrocene]dichloropalladium(II) dichloromethane complex.

The base used is preferably an alkali metal carbonate, an alkali metal phosphate, or an alkali metal alkoxide, more preferably cesium carbonate, potassium carbonate, or potassium phosphate n-hydrate.

The solvent used is preferably an aliphatic hydrocarbon, an aromatic hydrocarbon, an ether, water, or a mixture thereof, more preferably a mixed solvent of 1,4-dioxane and water, or a mixed solvent of 1,2-dimethoxyethane and water.

The reaction temperature is preferably room temperature to 120° C., more preferably 80° C. to 100° C.

The reaction time is 2 hours to 12 hours, preferably 4 hours.

Step A-3 is the step of reacting compound (1) with compound (4) to produce compound (6). This step can be carried out in the same way as in the step A-2.

Step A-4 is the step of reacting the compound (6) obtained in the step A-3 with compound (2) to produce compound (5). This step can be carried out in the same way as in the step A-1.

Step A-5 is the step of subjecting the compound (5) obtained in the step A-2 or the step A-4 to hydrolysis reaction under basic conditions to produce compound (Ia).

The base used is preferably an alkali metal hydroxide, more preferably sodium hydroxide or potassium hydroxide.

The solvent used is preferably an ether, an alcohol, water, or a mixture thereof, more preferably a mixed solvent of tetrahydrofuran and water, or methanol and water.

The reaction temperature is preferably room temperature to 50° C.

The reaction time is 30 minutes to 12 hours, preferably 2 hours.

[Manufacture Method 2]

Compound (Ib) represented by the general formula (I) wherein $R^5$ represents a C1-C6 alkyl group, a C1-C6 haloalkyl group, or a C1-C6 alkoxy group substituted by one tetrazolyl group can be produced by, for example, the following method:

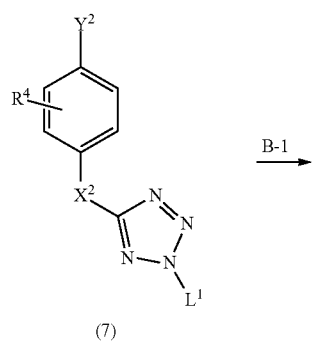
(7)

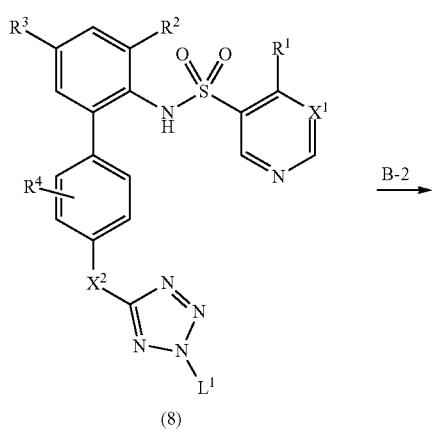
(8)

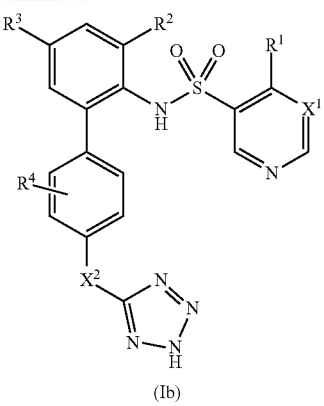
(Ib)

In the structural formulas of the compounds in [manufacture method 2] described above, $R^1$, $R^2$, $R^3$, $R^4$, $X^1$, and $X^2$ are as defined in the general formula (I) and [manufacture method 1]; and $L^1$ is a protective group for the tetrazole generally used, for example, a trityl group or a tetrahydropyranyl group.

Step B-1 can be carried out in the same way as in the steps A-1 and A-2 or the steps A-3 and A-4 in [manufacture method 1]. The compound (7) is commercially available or can be easily prepared from a compound known in the art.

Step B-2 is the step of deprotecting the protective group ($L^1$) for the tetrazole on the compound (8) obtained in the step B-1 to produce compound (Ib).

The deprotection reaction of this step is not particularly limited as long as the deprotection reaction does not influence the other parts of the compound. The reaction differs depending on the protective group used and can be carried out according to a routine method, for example, a method described in T. W. Greene, P. G. M. Wuts, Protective Groups in Organic Synthesis. Fourth Edition, 2007, John Wiley & Sons, Inc. Preferably, $L^1$ is a tetrahydropyranyl group, and the deprotection reaction thereof may be carried out under acidic conditions.

Examples of the solvent used include aliphatic hydrocarbons, aromatic hydrocarbons, halogenated hydrocarbons, ethers, and water. The solvent is preferably tetrahydrofuran or a mixed solvent of methanol and water.

Examples of the acid catalyst used include inorganic acids, organic acids and organic sulfonic acids. The acid catalyst is preferably hydrochloric acid.

The reaction temperature is preferably room temperature to 50° C.

The reaction time is 1 hour to 12 hours, preferably 5 hours.

[Manufacture Method 3]

Compound (Ic) represented by the general formula (I) wherein $R^5$ represents a C1-C6 alkylamino group (wherein the alkylamino group is optionally substituted by one group selected from a C1-C3 alkylsulfonyl group, a carboxy group and a tetrazolyl group) can be produced by, for example, the following method:

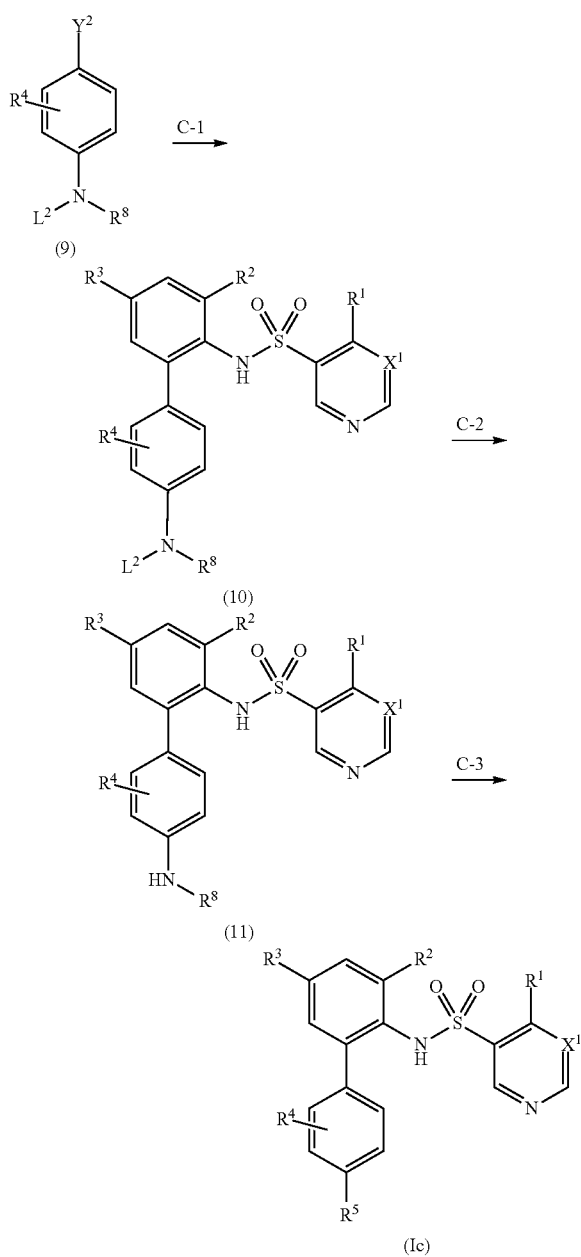

In the structural formulas of the compounds in [manufacture method 3] described above, $R^1$, $R^2$, $R^3$, $R^4$, $R^5$, $X^1$, and $Y^2$ are as defined in the general formula (I), [manufacture method 1], and [manufacture method 2]; $R^8$ is a C1-C6 alkyl group (wherein the alkyl group is optionally substituted by one group selected from a protected carboxy group and a tetrazolyl group); and $L^2$ is a protective group for the amino group generally used. Examples thereof include a tert-butoxycarbonyl group.

Step C-1 can be carried out in the same way as in the step B-1 in [manufacture method 2]. The compound (9) is commercially available or can be easily prepared from a compound known in the art.

Step C-2 is the step of deprotecting the protective group ($L^2$) for the amino group on the compound (10) obtained in the step C-1 to produce compound (11).

The deprotection reaction of this step is not particularly limited as long as the deprotection reaction does not influence the other parts of the compound. The reaction differs depending on the protective group used and can be carried out according to a routine method, for example, a method described in T. W. Greene, P. G. M. Wuts, Protective Groups in Organic Synthesis. Fourth Edition, 2007, John Wiley & Sons, Inc. Preferably, $L^2$ is a tert-butoxycarbonyl group, and the deprotection reaction thereof may be carried out under acidic conditions.

Examples of the solvent used preferably include aliphatic hydrocarbons, aromatic hydrocarbons, halogenated hydrocarbons, and ethers. The solvent is more preferably dichloromethane.

Examples of the acid catalyst used preferably include inorganic acids, organic acids and organic sulfonic acids. The acid catalyst is more preferably trifluoroacetic acid or hydrochloric acid.

The reaction temperature is preferably 0° C. to room temperature.

The reaction time is preferably 30 minutes to 5 hours, more preferably 2 hours.

Step C-3 is the step of deprotecting the compound (11) obtained in the step C-2 to obtain compound (Ic). This step can be carried out in the same way as in the step A-5 or the step B-2.

When the compound represented by the general formula (I) of the present invention or the pharmacologically acceptable salt thereof is used as a pharmaceutical, the compound or the salt can be administered alone (i.e., as a bulk) or can be administered orally as an appropriate pharmaceutically acceptable preparation such as a tablet, a capsule, granules, a powder, or a syrup or parenterally as an appropriate pharmaceutically acceptable preparation such as an injection, a suppository, or a patch (preferably orally).

These preparations are produced by well-known methods using additives such as excipients, binders, disintegrants, lubricants, emulsifiers, stabilizers, corrigents, diluents, solvents for injections, oleaginous bases, and water-soluble bases.

Examples of the excipients can include organic excipients and inorganic excipients. Examples of the organic excipients can include: sugar derivatives such as lactose, saccharose, glucose, mannitol, and sorbitol; starch derivatives such as corn starch, potato starch, α-starch, dextrin, and carboxymethyl starch; cellulose derivatives such as crystalline cellulose, low-substituted hydroxypropylcellulose, hydroxypropylmethylcellulose, carboxymethylcellulose, carboxymethylcellulose calcium, and internally crosslinked carboxymethylcellulose sodium; gum arabic; dextran; and pullulan. Examples of the inorganic excipients can include: light anhydrous silicic acid and silicate derivatives such as synthetic aluminum silicate and calcium silicate; phosphates such as calcium phosphate; and sulfates such as calcium sulfate.

Examples of the binders can include: the excipients listed above; gelatin; polyvinylpyrrolidone; and polyethylene glycol.

Examples of the disintegrants can include: the excipients listed above; chemically modified starch or cellulose derivatives such as croscarmellose sodium and carboxymethyl starch sodium; and cross-linked polyvinylpyrrolidone.

Examples of the lubricants can include: talc; stearic acid; stearic acid metal salts such as calcium stearate and magnesium stearate; colloidal silica; waxes such as bees wax and spermaceti; boric acid; glycol; D,L-leucine; carboxylic acids such as fumaric acid and adipic acid; carboxylic acid sodium salts such as sodium benzoate; sulfates such as sodium sulfate; lauryl sulfates such as sodium lauryl sulfate and magnesium lauryl sulfate; silicic acids such as silicic anhydride and silicic acid hydrate; and the starch derivatives listed as the excipients.

Examples of the emulsifiers can include: colloidal clay such as bentonite and veegum; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester.

Examples of the stabilizers can include: p-hydroxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of the corrigents can include sweeteners, acidulants, and flavors usually used.

Examples of the diluents can include water, ethanol, propylene glycol, ethoxylated isostearyl alcohol, and polyoxyethylene sorbitan fatty acid esters.

Examples of the solvents for injections can include water, ethanol, and glycerin.

Examples of the oleaginous bases can include cacao butter, laurin butter, coconut oil, palm kernel oil, camellia oil, liquid paraffin, white petrolatum, purified lanoline, glycerin monostearate, polyoxyethylene hydrogenated castor oil, sorbitan fatty acid ester, sucrose fatty acid ester, stearyl alcohol, and cetanol.

Examples of the water-soluble bases can include glycerin, polyethylene glycol, ethanol, and purified water.

The dose of the compound represented by the general formula (I) of the present invention or the pharmacologically acceptable salt thereof serving as an active ingredient differs depending on the symptoms and age of a patient. The single dose thereof is 0.001 mg/kg (preferably 0.01 mg/kg) as the lower limit and 10 mg/kg (preferably 1 mg/kg) as the upper limit for oral administration and 0.001 mg/kg (preferably 0.01 mg/kg) as the lower limit and 10 mg/kg (preferably 1 mg/kg) as the upper limit for parenteral administration and can be administered to an adult once to six times a day according to the symptoms.

The compound of the present invention can be used in combination with any of various therapeutic or prophylactic agents for the aforementioned disease for which the compound of the present invention is probably effective. In this combined use, the compound of the present invention and the agent may be administered simultaneously, separately but continuously, or at the desired time interval. The preparations to be administered simultaneously may be formulated as a combination drug or formulated as separate preparations.

The biaryl derivative or the pharmacologically acceptable salt thereof, which is the compound of the present invention, has an excellent TNAP inhibitory effect and is useful as a therapeutic or prophylactic agent for pseudoxanthoma elasticum (PXE), generalized arterial calcification of infancy (GACI), craniometaphyseal dysplasia (CMD), ossification of the yellow ligament (OYL), arterial calcification due to deficiency of CD73 (ACDC), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, or peritoneal calcification. Moreover, the compound of the present invention has low toxicity and excellent safety and as such, is very useful as a pharmaceutical.

DETAILED DESCRIPTION OF THE PREFERRED EMBODIMENTS

Hereinafter, the present invention will be described in more detail with reference to Examples. However, the scope of the present invention is not intended to be limited by them.

The chemical structural formulas described in Examples represent the chemical structures of corresponding compounds in a free form.

Elution in column chromatography in Examples was carried out under observation by thin layer chromatography (TLC). In the TLC observation, silica gel 60F$_{254}$ manufactured by Merck KGaA was used as a TLC plate; a solvent used as an eluting solvent in column chromatography was used as a developing solvent; and a UV detector or a chromogenic method using a coloring agent (e.g., a ninhydrin coloring solution, an anisaldehyde coloring solution, an ammonium phosphomolybdate coloring solution, a cerium ammonium nitrate (CAM) coloring solution, or an alkaline permanganate coloring solution) was used as a detection method. Silica gel SK-85 (230-400 mesh) also manufactured by Merck KGaA, silica gel 60 N (40-50 μm) manufactured by Kanto Chemical Co., Inc., or Chromatorex NH (200-350 mesh) manufactured by Fuji Silysia Chemical Ltd. was used as silica gel for columns. In addition to general column chromatography, an automatic chromatography apparatus (Purif-α2 or Purif-espoir2) manufactured by Shoko Scientific Co., Ltd., an automatic chromatography apparatus (W-Prep 2XY) manufactured by Yamazen Corp., an automatic chromatography apparatus (Isolera One) manufactured by Biotage Japan Ltd., or an automatic chromatography apparatus (CombiFlash Rf) manufactured by Teledyne Isco, Inc. was appropriately used. The eluting solvent was determined on the basis of the TLC observation.

In Examples, nuclear magnetic resonance ($^1$H NMR) spectra were indicated by chemical shift δ values (ppm) determined with tetramethylsilane as a standard. Splitting patterns were indicated by s for singlet, d for doublet, t for triplet, q for quartet, m for multiplet, and br for broad. Mass spectrometry (hereinafter, referred to as MS) was conducted by the electron ionization (EI), electron spray ionization (ESI), atmospheric pressure chemical ionization (APCI), electron spray atmospheric pressure chemical ionization (ES/APCI), or fast atom bombardment (FAB) method.

In each step of Examples, the adjustment of a reaction solution and reaction were carried out at room temperature unless the temperature is otherwise specified.

EXAMPLES

Example 1

({3',5'-Dichloro-2'-[(pyridine-3-sulfonyl)amino][1,1'-biphenyl]-4-yl}oxy)acetic acid <1-a> Methyl [(2'-amino-3',5'-dichloro[1,1'-biphenyl]-4-yl)oxy]acetate To a solution of methyl 2-[4-(4,4,5,5-tetramethyl-1,3,2-dioxaborolan-2-yl)phenoxy]acetate (6.82 g, 23.3 mmol), 2-bromo-4,6-dichloro-aniline (7.03 g, 29.2 mmol), and potassium phosphate, tribasic (12.4 g, 58.4 mmol) in 1,2-dimethoxyethane (60 mL) and water (15 mL), [1,1'-bis(diphenylphosphino)ferrocene]dichloropalladium(II), complex with dichloromethane (1.91 g, 2.33 mmol) was added under the nitrogen atmosphere. Subsequently, the mixture was heated and stirred at 90° C. for 3 hours. After cooling to room temperature, the solvent was distilled off under reduced pressure, and the obtained residue was subsequently diluted with ethyl acetate and water. After extraction with ethyl acetate, combined organic layers were washed with water and saturated saline in this order and dried over anhydrous sodium sulfate. The desiccant was filtered off, and then, the solvent was distilled off under reduced pressure to obtain a viscous solid. This solid was suspended in dichloromethane, and insoluble matter was filtered off through Celite. The solvent in the filtrate was distilled off under reduced pressure to obtain a crude product as a viscous oil. This oil was purified by silica gel column chromatography [eluting solvent: hexane/ethyl acetate=89/11-68/32 (V/V))] to obtain a solid. This solid was collected by filtration with diisopropyl ether and washed to obtain the title compound (3.55 g, 10.9 mmol, 47%) as a solid.

$^1$H-NMR (CDCl$_3$) δ: 3.84 (3H, s), 4.12 (2H, br s), 4.69 (2H, s), 6.98-7.00 (3H, m), 7.24 (1H, d, J=2.4 Hz), 7.31-7.37 (2H, m).

<1-b> Methyl ({3',5'-dichloro-2'-[(pyridine-3-sulfonyl)amino][1,1'-biphenyl]-4-yl}oxy)acetate To a solution of methyl 2-[4-(2-amino-3,5-dichloro-phenyl)phenoxy]acetate (200 mg, 0.613 mmol) in pyridine (1.5 mL, 19.1 mmol), pyridine-3-sulfonyl chloride (109 mg, 0.613 mmol) dissolved in a small amount of dichloromethane was added, and the mixture was stirred at room temperature for 15 minutes and then heated and stirred at 60° C. for 1 hour. Subsequently, the temperature was raised to 70° C., and the reaction mixture was heated and stirred for 1 hour. Pyridine-3-sulfonyl chloride (111 mg, 0.613 mmol) was further added thereto. The temperature was raised to 90° C., and the mixture was heated and stirred for 1 hour. Pyridine-3-sulfonyl chloride (232 mg, 1.23 mmol) was further added thereto again, and the mixture was heated and stirred at the same temperature as above for 1 hour. After cooling to room temperature, the solvent was distilled off under reduced pressure, and the obtained residue was purified by silica gel column chromatography [eluting solvent: hexane/ethyl acetate=29/71-8/92 (V/V))] and then further purified by reverse-phase silica gel column chromatography [eluting solvent: water/acetonitrile=80/20-10/90 (V/V))] to obtain the title compound (57.7 mg, 0.123 mmol, 20.1%) in an amorphous form.

$^1$H-NMR (CDCl$_3$) δ: 3.85 (3H, s), 4.65 (2H, s), 6.41 (1H, s), 6.72-6.77 (2H, m), 7.13-7.17 (2H, m), 7.22 (1H, d, J=2.4 Hz), 7.24-7.28 (1H, m), 7.42 (1H, d, J=2.4 Hz), 7.62-7.67 (1H, m), 8.66-8.70 (2H, m).
LCMS (ES): m/z 466.0 [M+H]$^+$.

<1-c> ({3',5'-Dichloro-2'-[(pyridine-3-sulfonyl)amino][1,1'-biphenyl]-4-yl}oxy)acetic acid To a solution of methyl ({3',5'-dichloro-2'-[(pyridine-3-sulfonyl)amino][1,1'-biphenyl]-4-yl}oxy)acetate (56.2 mg, 0.120 mmol) in ethanol (2 mL), a 1 mol/L sodium hydroxide solution (1 mL, 1.0 mmol) was added, and the mixture was stirred at room temperature for 1 hour. The solvent was distilled off under reduced pressure, and the obtained residue was diluted with water, followed by the addition of 1 mol/L hydrochloric acid (1 mL, 1.0 mmol). The precipitated solid was collected by filtration, washed with water and diisopropyl ether, and then dried under reduced pressure to obtain the title compound (30.5 mg, 0.0673 mmol, 56%) as a solid.

Example 2

2-({3',5'-Dichloro-2'-[(5-methylpyridine-3-sulfonyl)amino][1,1'-biphenyl]-4-yl}oxy)-2-methylpropanoic acid <2-a> Ethyl 2-methyl-2-[4-(4,4,5,5-tetramethyl-1,3,2-dioxaborolan-2-yl)phenoxy]propanoate To a solution of 4-(4,4,5,5-tetramethyl-1,3,2-dioxaborolan-2-yl)phenol (1.00 g, 4.54 mmol) in acetonitrile (9 mL), cesium carbonate (2.37 g, 7.27 mmol) was added, and the mixture was stirred. Subsequently, 2-bromoisobutyric acid ethyl ester (1.33 g, 6.82 mmol) was added thereto, and the mixture was heated to reflux for 9 hours. After cooling to room temperature, the reaction solution was diluted with ethyl acetate, and the organic layer was washed with water and saturated saline in this order and dried over anhydrous sodium sulfate. The desiccant was filtered off, and then, the solvent was distilled off under reduced pressure. The obtained residue was purified by silica gel column chromatography [eluting solvent: hexane/ethyl acetate=100/0-80/20 (V/V))] to obtain the title compound (830 mg, 2.48 mmol, 55%) as a viscous oil.

$^1$H-NMR (CDCl$_3$) δ: 1.22 (3H, t, J=7.0 Hz), 1.33 (12H, s), 1.62 (6H, s), 4.22 (2H, q, J=7.1 Hz), 6.78-6.82 (2H, m), 7.65-7.72 (2H, m).

<2-b> Ethyl 2-[(2'-amino-3',5'-dichloro[1,1'-biphenyl]-4-yl)oxy]-2-methylpropanoate The title compound (794 mg, 2.16 mmol, 87%) was obtained as an oil in the same way as in Example (1-a) using ethyl 2-methyl-2-[4-(4,4,5,5-tetramethyl-1,3,2-dioxaborolan-2-yl)phenoxy]propanoate (828 mg, 2.48 mmol) obtained in Example (2-a) and 2-bromo-4,6-dichloro-aniline (748 mg, 3.10 mmol).

$^1$H-NMR (CDCl$_3$) δ: 1.27 (3H, t, J=7.3 Hz), 1.64 (6H, s), 4.12 (2H, br s), 4.27 (2H, q, J=7.1 Hz), 6.89-6.94 (2H, m), 6.99 (1H, d, J=2.4 Hz), 7.23-7.30 (3H, m).
LCMS (ES): m/z 368 [M+H]$^+$.

<2-c> Ethyl 2-({3',5'-dichloro-2'-[(5-methylpyridine-3-sulfonyl)amino][1,1'-biphenyl]-4-yl}oxy)-2-methylpropanoate The title compound (52.7 mg, 0.101 mmol, 18%) was obtained as a solid in the same way as in Example (1-b) using ethyl 2-[(2'-amino-3',5'-dichloro[1,1'-biphenyl]-4-yl)oxy]-2-methylpropanoate (207 mg, 0.562 mmol) obtained in Example (2-b) and 5-methylpyridine-3-sulfonyl chloride (253 mg, 1.32 mmol).
LCMS (ES): m/z 368 [M+H]$^+$.

<2-d> 2-({3',5'-Dichloro-2'-[(5-methylpyridine-3-sulfonyl)amino][1,1'-biphenyl]-4-yl}oxy)-2-methylpropanoic acid The title compound (38.9 mg, 0.0785 mmol, 78%) was obtained as a solid in the same way as in Example (1-c) using ethyl 2-({3',5'-dichloro-2'-[(5-methylpyridine-3-sulfonyl)amino][1,1'-biphenyl]-4-yl}oxy)-2-methylpropanoate (52.5 mg, 0.100 mmol) obtained in Example (2-c).

Example 3

2-({5'-Chloro-3'-fluoro-2'-[(5-methylpyridine-3-sulfonyl)amino][1,1'-biphenyl]-4-yl}oxy)-2-methylpropanoic acid <3-a> Ethyl 2-[(2'-amino-5'-chloro-3'-fluoro[1,1'-biphenyl]-4-yl)oxy]-2-methylpropanoate The title compound (467 mg, 1.33 mmol, 93%) was obtained as a solid in the same way as in Example (1-a) using ethyl 2-methyl-2-[4-(4,4,5,5-tetramethyl-1,3,2-dioxaborolan-2-yl)phenoxy]propanoate (522 mg, 1.57 mmol) obtained in Example (2-a) and 2-bromo-4-chloro-6-fluoroaniline (321 mg, 1.43 mmol).
$^1$H-NMR (CDCl$_3$) δ: 1.27 (3H, t, J=7.0 Hz), 1.64 (6H, s), 3.78 (2H, br s), 4.27 (2H, q, J=7.1 Hz), 6.89-6.94 (3H, m), 6.99 (1H, dd, J=10.3, 2.4 Hz), 7.28-7.32 (2H, m).
LCMS (ES): m/z 352 [M+H]$^+$.

<3-b> Ethyl 2-({5'-chloro-3'-fluoro-2'-[(5-methylpyridine-3-sulfonyl)amino][1,1'-biphenyl]-4-yl}oxy)-2-methylpropanoate The title compound (72.6 mg, 0.101 mmol, 33%) was obtained as a viscous oil in the same way as in Example (1-b) using ethyl 2-[(2'-amino-5'-chloro-3'-fluoro[1,1'-biphenyl]-4-yl)oxy]-2-methylpropanoate (151 mg, 0.429 mmol) obtained in Example (3-a) and 5-methylpyridine-3-sulfonyl chloride (98.2 mg, 0.512 mmol).
$^1$H-NMR (CDCl$_3$) δ: 1.28 (3H, t, J=7.0 Hz), 1.64 (6H, s), 2.36 (3H, s), 4.26 (2H, q, J=7.1 Hz), 6.22 (1H, br s), 6.77-6.82 (2H, m), 7.06-7.14 (4H, m), 7.63-7.65 (1H, br m), 8.56 (1H, d, J=1.2 Hz), 8.63 (1H, d, J=1.8 Hz).
LC-MS (ES): m/z 507 [M+H]$^+$.

<3-c> 2-({5'-Chloro-3'-fluoro-2'-[(5-methylpyridine-3-sulfonyl)amino][1,1'-biphenyl]-4-yl}oxy)-2-methylpropanoic acid The title compound (62.8 mg, 0.131 mmol, 93%) was obtained as a solid in the same way as in Example (1-c) using ethyl 2-({5'-chloro-3'-fluoro-2'-[(5-methylpyridine-3-sulfonyl)amino][1,1'-biphenyl]-4-yl}oxy)-2-methylpropanoate (71.1 mg, 0.140 mmol) obtained in Example (3-b).

Example 4

3-{5'-Chloro-3'-fluoro-2'-[(5-methylpyridine-3-sulfonyl)amino][1,1'-biphenyl]-4-yl}propanoic acid <4-a> Ethyl 3-(2'-amino-5'-chloro-3'-fluoro[1,1'-biphenyl]-4-yl)propanoate The title compound (690 mg, 2.14 mmol, 77.6%) was obtained as an oil in the same way as in Example (1-a) using 2-bromo-4-chloro-6-fluoroaniline (620 mg, 2.76 mmol) and [4-(2-ethoxycarbonylethyl)phenyl]boronic acid (680 mg, 3.04 mmol).
LCMS (ES): m/z 322 [M+H]$^+$.

<4-b> Ethyl 3-{5'-chloro-3'-fluoro-2'-[(5-methylpyridine-3-sulfonyl)amino][1,1'-biphenyl]-4-yl}propanoate The title compound (105 mg, 0.220 mmol, 41.7%) was obtained as an oil in the same way as in Example (1-b) using ethyl 3-(2'-amino-5'-chloro-3'-fluoro[1,1'-biphenyl]-4-yl)propanoate (170 mg, 0.528 mmol) obtained in Example (4-a) and 5-methylpyridine-3-sulfonyl chloride (101 mg, 0.528 mmol).
$^1$H-NMR (CDCl$_3$) δ: 1.27 (3H, t, J=7.1 Hz), 2.34 (3H, s), 2.65 (2H, t, J=7.6 Hz), 2.97 (2H, t, J=7.8 Hz), 4.17 (2H, q, J=7.0 Hz), 6.35 (1H, s), 7.10 (1H, dd, J=2.4, 1.5 Hz), 7.17-7.13 (3H, m), 7.19 (2H, d, J=7.8 Hz), 7.65 (1H, s), 8.54 (1H, d, J=1.5 Hz), 8.60 (1H, d, J=2.0 Hz).
LCMS (ES): m/z 477 [M+H]$^+$.

<4-c> 3-{5'-Chloro-3'-fluoro-2'-[(5-methylpyridine-3-sulfonyl)amino][1,1'-biphenyl]-4-yl}propanoic acid The title compound (90 mg, 0.200 mmol, 91.1%) was obtained as a solid in the same way as in Example (1-c) using ethyl 3-{5'-chloro-3'-fluoro-2'-[(5-methylpyridine-3-sulfonyl)amino][1,1'-biphenyl]-4-yl}propanoate (105 mg, 0.220 mmol) obtained in Example (4-b).

Example 5

N-{5'-Chloro-3'-fluoro-2'-[(5-methylpyridine-3-sulfonyl)amino][1,1'-biphenyl]-4-yl}glycine <5-a> Ethyl N-(tert-butoxycarbonyl)-N-[4-(4,4,5,5-tetramethyl-1,3,2-dioxaborolan-2-yl)phenyl]glycinate To a solution of t-butyl N-[4-(4,4,5,5-tetramethyl-1,3,2-dioxaborolan-2-yl)phenyl]carbamate (1.0 g, 3.1 mmol) in N,N-dimethylformamide (10 mL), cesium carbonate (2.1 g, 6.3 mmol) and ethyl iodoacetate (0.45 ml, 3.8 mmol) were added, and the mixture was stirred at room temperature for 16 hours. The reaction solution was concentrated, and dichloromethane was added to the obtained residue. The precipitated solid was filtered off. The mother liquor was concentrated again, and the obtained residue was purified by silica gel column chromatography [eluting solvent: hexane/ethyl acetate=100/0-70/30 (V/V))] to obtain the title compound (2.14 g, 3.26 mmol, 66%) as an oil.
$^1$H-NMR (CDCl$_3$) δ: 1.28 (3H, t, J=7.1 Hz), 1.34 (12H, s), 1.44 (9H, s), 4.22 (2H, q, J=7.1 Hz), 4.30 (2H, s), 7.27-7.31 (2H, m), 7.77 (2H, d, J=8.3 Hz).
LCMS (ES): m/z 306 [M+H−BOC]$^+$.

<5-b> Ethyl N-(2'-amino-5'-chloro-3'-fluoro[1,1'-biphenyl]-4-yl)-N-(tert-butoxycarbonyl)glycinate The title compound (665 mg, 1.57 mmol, 75.1%) was obtained as an oil in the same way as in Example (1-a) using ethyl N-(tert-butoxycarbonyl)-N-[4-(4,4,5,5-tetramethyl-1,3,2-dioxaborolan-2-yl)phenyl]glycinate (1.15 g, 2.51 mmol) obtained in Example (5-a) and 2-bromo-4-chloro-6-fluoroaniline (470 mg, 2.09 mmol).
$^1$H-NMR (CDCl$_3$) δ: 1.33 (3H, t, J=7.1 Hz), 1.50 (9H, s), 3.83 (2H, s), 4.27 (2H, q, J=7.2 Hz), 4.33 (2H, s), 6.93 (1H, s), 7.03 (1H, dd, J=10.3, 2.4 Hz), 7.36-7.48 (4H, m).
LCMS (ES): m/z 323 [M+H−BOC]$^+$.

<5-c> Ethyl N-(tert-butoxycarbonyl)-N-{5'-chloro-3'-fluoro-2'-[(5-methylpyridine-3-sulfonyl)amino][1,1'-biphenyl]-4-yl}glycinate The title compound (91 mg, 0.157 mmol, 38%) was obtained as an oil in the same way as in Example (1-b) using ethyl N-(2'-amino-5'-chloro-3'-fluoro[1,1'-biphenyl]-4-yl)-N-(tert-butoxycarbonyl)glycinate (175 mg, 0.414 mmol) obtained in Example (5-b).

$^1$H-NMR (CDCl$_3$) δ: 1.34 (3H, t, J=7.1 Hz), 1.49 (9H, s), 2.37 (3H, s), 4.28 (2H, q, J=7.0 Hz), 4.34 (2H, s), 6.28 (1H, s), 7.11 (1H, s), 7.14 (1H, dd, J=9.3, 2.4 Hz), 7.21 (2H, d, J=8.8 Hz), 7.32 (2H, d, J=8.3 Hz), 7.72 (1H, s), 8.55 (1H, s), 8.59 (1H, d, J=2.0 Hz).

LCMS (ES): m/z 578 [M+H]$^+$.

<5-d> Ethyl N-{5'-chloro-3'-fluoro-2'-[(5-methylpyridine-3-sulfonyl)amino][1,1'-biphenyl]-4-yl}glycinate Ethyl N-(tert-butoxycarbonyl)-N-{5'-chloro-3'-fluoro-2'-[(5-methylpyridine-3-sulfonyl)amino][1,1'-biphenyl]-4-yl}glycinate (91 mg, 0.157 mmol) obtained in Example (5-c) was dissolved in dichloromethane (5 mL). To the solution, trifluoroacetic acid (2 mL) was added at room temperature, and the mixture was stirred for 12 hours. A saturated aqueous solution of sodium bicarbonate was added to the reaction solution, followed by extraction with dichloromethane and ethyl acetate. The organic layer was concentrated, and the obtained residue was purified by silica gel column chromatography [eluting solvent: hexane/ethyl acetate=70/30-0/100 (V/V)] to obtain the title compound (48 mg, 0.075 mmol, 64%) as an oil.

$^1$H-NMR (CDCl$_3$) δ: 1.34 (3H, t, J=7.1 Hz), 2.32 (3H, s), 3.91 (2H, s), 4.29 (2H, q, J=7.2 Hz), 6.31-6.38 (1H, m), 6.52 (2H, dd, J=6.3, 2.0 Hz), 7.03 (2H, dd, J=6.3, 2.0 Hz), 7.11-7.06 (2H, m), 7.62 (1H, s), 8.52 (1H, s), 8.62 (1H, s).

LCMS (ES): m/z 478 [M+H]$^+$.

<5-e> N-{5'-Chloro-3'-fluoro-2'-[(5-methylpyridine-3-sulfonyl)amino][1,1'-biphenyl]-4-yl}glycine The title compound (28 mg, 0.062 mmol, 62%) was obtained as a solid in the same way as in Example (1-c) using ethyl N-{5'-chloro-3'-fluoro-2'-[(5-methylpyridine-3-sulfonyl)amino][1,1'-biphenyl]-4-yl}glycinate (48 mg, 0.10 mmol) obtained in Example (5-d).

Example 6

N-{5-Chloro-3-fluoro-4'-[(2H-tetrazol-5-yl)methoxy][1,1'-biphenyl]-2-yl}-5-methylpyridine-3-sulfonamide <6-a> 2-(Oxan-2-yl)-5-{[4-(4,4,5,5-tetramethyl-1,3,2-dioxaborolan-2-yl)phenoxy]methyl}-2H-tetrazole 5-Chloromethyl-1H-tetrazole (1.1 g, 8.44 mmol) was dissolved in acetone (20 mL). To the solution, 3,4-dihydro-2H-pyran (1.2 ml, 12.7 mmol) and pyridinium p-toluenesulfonate (52 mg, 0.169 mmol) were added, and the mixture was stirred at 50° C. for 7 hours. 4-(4,4,5,5-Tetramethyl-1,3,2-dioxaborolan-2-yl)phenol (1.3 g, 5.91 mmol) and cesium carbonate (6.6 g, 21.1 mmol) were added to the reaction solution, and the mixture was stirred at 60° C. for 3 hours. Insoluble matter in the reaction solution was filtered off, and the mother liquor was concentrated. The obtained residue was purified by silica gel column chromatography [eluting solvent: hexane/ethyl acetate=100/0-70/30 (V/V)] to obtain the title compound (2.14 g, 3.26 mmol, 66%) as an oil.

$^1$H-NMR (CDCl$_3$) δ: 1.33 (12H, s), 1.69-1.82 (3H, m), 2.10-2.21 (2H, m), 2.37-2.49 (1H, m), 3.84-3.76 (1H, m), 4.02-3.95 (1H, m), 5.37 (2H, s), 6.01-6.05 (1H, m), 7.03 (2H, d, J=8.6 Hz), 7.76 (2H, d, J=8.6 Hz).

LCMS (ES): m/z 303 [M+H−THP]$^+$.

<6-b> 5-Chloro-3-fluoro-4'-{[2-(oxan-2-yl)-2H-tetrazol-5-yl]methoxy}[1,1'-biphenyl]-2-amine The title compound (790 mg, 1.96 mmol, 35.3%) was obtained as an oil in the same way as in Example (1-a) using 2-(oxan-2-yl)-5-{[4-(4,4,5,5-tetramethyl-1,3,2-dioxaborolan-2-yl)phenoxy]methyl}-2H-tetrazole (2.14 g, 5.54 mmol) obtained in Example (6-a).

$^1$H-NMR (CDCl$_3$) δ: 1.72-1.82 (3H, m), 2.22-2.11 (2H, m), 2.41-2.50 (1H, m), 3.75-3.84 (3H, m), 4.00-4.03 (1H, m), 5.40 (2H, s), 6.06 (1H, dd, J=7.8, 2.9 Hz), 6.91 (1H, t, J=1.7 Hz), 7.00 (1H, dd, J=10.3, 2.4 Hz), 7.13 (2H, dt, J=9.3, 2.6 Hz), 7.37 (2H, dt, J=9.3, 2.6 Hz).

<6-c> N-(5-Chloro-3-fluoro-4'-{[2-(oxan-2-yl)-2H-tetrazol-5-yl]methoxy}[1,1'-biphenyl]-2-yl)-5-methylpyridine-3-sulfonamide and N-(5-chloro-3-fluoro-4'-{[2-(oxan-2-yl)-2H-tetrazol-5-yl]methoxy}[1,1'-biphenyl]-2-yl)-5-methyl-N-(5-methylpyridine-3-sulfonyl)pyridine-3-sulfonamide A mixture of the two title compounds (584 mg) was obtained as an oil in the same way as in Example (1-b) using 5-chloro-3-fluoro-4'-{[2-(oxan-2-yl)-2H-tetrazol-5-yl]methoxy}[1,1'-biphenyl]-2-amine (460 mg, 1.14 mmol) obtained in Example (6-b).

LCMS (ES): m/z 559 [M+H]$^+$, 715 [M+H]$^+$.

<6-d> N-{5-Chloro-3-fluoro-4'-[(2H-tetrazol-5-yl)methoxy][1,1'-biphenyl]-2-yl}-5-methylpyridine-3-sulfonamide The mixture of N-(5-chloro-3-fluoro-4'-{[2-(oxan-2-yl)-2H-tetrazol-5-yl]methoxy}[1,1'-biphenyl]-2-yl)-5-methylpyridine-3-sulfonamide and N-(5-chloro-3-fluoro-4'-{[2-(oxan-2-yl)-2H-tetrazol-5-yl]methoxy}[1,1'-biphenyl]-2-yl)-5-methyl-N-(5-methylpyridine-3-sulfonyl)pyridine-3-sulfonamide (584 mg) obtained in Example (6-c) was dissolved in a mixed solvent of methanol (5 mL) and tetrahydrofuran (5 mL). To the solution, a 1 mol/L sodium hydroxide solution (2.0 ml, 2.0 mmol) was added, and the mixture was stirred at room temperature for 4 hours. 1 mol/L hydrochloric acid (4.0 ml, 4.0 mmol) was added to the reaction solution, and the mixture was stirred at 50° C. for 2 hours. The reaction solution was neutralized by the addition of a 1 mol/L sodium hydroxide solution (2.0 ml, 2.0 mmol), followed by extraction with dichloromethane and ethyl acetate. The organic layer was concentrated under reduced pressure, and the obtained residue was purified by reverse-phase silica gel column chromatography [eluting solvent: water/acetonitrile=80/20-10/90 (V/V)] to obtain the title compound (270 mg, 0.569 mmol, 50.0% for 2 steps) as a solid.

Example 7

2-({5'-Chloro-2'-[(5-ethylpyridine-3-sulfonyl)amino]-3'-fluoro[1,1'-biphenyl]-4-yl}oxy)-2-methylpropanoic acid <7-a> Ethyl 2-({5'-chloro-2'-[(5-ethylpyridine-3-sulfonyl)amino]-3'-fluoro[1,1'-biphenyl]-4-yl}oxy)-2-methylpropanoate The title compound (100 mg, 0.192 mmol, 51.9%) was obtained as a solid in the same way as in Example (1-b)

using ethyl 2-[(2'-amino-5'-chloro-3'-fluoro[1,1'-biphenyl]-4-yl)oxy]-2-methylpropanoate (130 mg, 0.370 mmol) obtained in Example (3-a) and 5-ethylpyridine-3-sulfonyl chloride (120 mg, 0.480 mmol).

$^1$H-NMR (CDCl$_3$) δ: 1.26 (3H, t, J=7.8 Hz), 1.28 (3H, t, J=6.8 Hz), 1.64 (6H, s), 2.70 (2H, q, J=7.6 Hz), 4.27 (2H, q, J=7.2 Hz), 6.21 (1H, s), 6.82 (2H, d, J=8.8 Hz), 7.12-7.08 (2H, m), 7.13 (2H, d, J=8.8 Hz), 7.72 (1H, s), 8.59 (1H, d, J=2.0 Hz), 8.66 (1H, d, J=2.4 Hz).

LCMS (ES): m/z 521 [M+H]$^+$.

<7-b> 2-({5'-Chloro-2'-[(5-ethylpyridine-3-sulfonyl)amino]-3'-fluoro[1,1'-biphenyl]-4-yl}oxy)-2-methylpropanoic acid The title compound (55 mg, 0.112 mmol, 58.1%) was obtained as a solid in the same way as in Example (1-c) using ethyl 2-({5'-chloro-2'-[(5-ethylpyridine-3-sulfonyl)amino]-3'-fluoro[1,1'-biphenyl]-4-yl}oxy)-2-methylpropanoate (100 mg, 0.191 mmol) obtained in Example (7-a).

Example 8

2-({5'-Chloro-2'-[(4,5-dimethylpyridine-3-sulfonyl)amino]-3'-fluoro[1,1'-biphenyl]-4-yl}oxy)-2-methylpropanoic acid <8-a> Ethyl 2-({5'-chloro-2'-[(4,5-dimethylpyridine-3-sulfonyl)amino]-3'-fluoro[1,1'-biphenyl]-4-yl}oxy)-2-methylpropanoate Ethyl 2-[(2'-amino-5'-chloro-3'-fluoro[1,1'-biphenyl]-4-yl)oxy]-2-methylpropanoate (11.7 g, 33.3 mmol) obtained in Example (3-a) was dissolved in pyridine (12 mL), and the reaction solution was heated to 70° C. Then, a solution of 4,5-dimethylpyridine-3-sulfonyl chloride (10.3 g, 50.0 mmol) in dichloromethane (100 mL) was added dropwise thereto over 1 hour. The mixture was stirred at 70° C. for 2 hours. Water was added to the reaction solution, followed by extraction with dichloromethane. The extract was purified by silica gel column chromatography [eluting solvent: hexane/ethyl acetate=80/20-50/50 (V/V)] to obtain the title compound (5.33 g, 10.2 mmol, 30.7%) as a solid.

$^1$H-NMR (CDCl$_3$) δ: 1.28 (3H, q, J=6.5 Hz), 1.63 (6H, s), 2.27 (3H, s), 2.36 (3H, s), 4.26 (2H, q, J=7.0 Hz), 6.22 (1H, s), 6.75 (2H, d, J=8.8 Hz), 7.06-7.01 (3H, m), 7.11 (1H, dd, J=9.3, 2.4 Hz), 8.44 (1H, s), 8.67 (1H, s).

LCMS (ES): m/z 521 [M+H]$^+$.

<8-b> 2-({5'-Chloro-2'-[(4,5-dimethylpyridine-3-sulfonyl)amino]-3'-fluoro[1,1'-biphenyl]-4-yl}oxy)-2-methylpropanoic acid The title compound (132 mg, 0.268 mmol, 89.4%) was obtained as a solid in the same way as in Example (1-c) using ethyl 2-({5'-chloro-2'-[(4,5-dimethylpyridine-3-sulfonyl)amino]-3'-fluoro[1,1'-biphenyl]-4-yl}oxy)-2-methylpropanoate (156 mg, 0.299 mmol) obtained in Example (8-a).

Example 9

Potassium 2-({5'-chloro-2'-[(4,5-dimethylpyridine-3-sulfonyl)amino]-3'-fluoro[1,1'-biphenyl]-4-yl}oxy)-2-methylpropanoate 2-({5'-Chloro-2'-[(4,5-dimethylpyridine-3-sulfonyl)amino]-3'-fluoro[1,1'-biphenyl]-4-yl}oxy)-2-methylpropanoic acid (101 mg, 0.205 mmol) obtained in Example 8 was dissolved in ethanol (2 mL). To the solution, a 0.5 mol/l solution of potassium hydroxide in ethanol (0.410 ml, 0.205 mmol) was added, and the mixture was stirred at room temperature for 20 minutes. The reaction solution was concentrated, and diethyl ether was added to the obtained residue. The precipitated solid was collected by filtration and then dried under reduced pressure at 50° C. to obtain the title compound (90.0 mg, 0.169 mmol, 82.7%) as a solid.

Example 10

Sodium 2-({5'-chloro-2'-[(4,5-dimethylpyridine-3-sulfonyl)amino]-3'-fluoro[1,1'-biphenyl]-4-yl}oxy)-2-methylpropanoate 2-({5'-Chloro-2'-[(4,5-dimethylpyridine-3-sulfonyl)amino]-3'-fluoro[1,1'-biphenyl]-4-yl}oxy)-2-methylpropanoic acid (101 mg, 0.205 mmol) obtained in Example 8 was dissolved in ethanol (2 mL). To the solution, a 2 mol/L sodium hydroxide solution (0.103 ml, 0.205 mmol) was added, and the mixture was stirred at room temperature for 20 minutes. The reaction solution was concentrated, and diethyl ether was added to the obtained residue. The precipitated solid was collected by filtration and then dried under reduced pressure at 50° C. to obtain the title compound (92.0 mg, 0.179 mmol, 87.2%) as a solid.

Example 11

{5'-Chloro-3'-fluoro-2'-[(5-methylpyridine-3-sulfonyl)amino][1,1'-biphenyl]-4-yl}acetic acid <11-a> Ethyl (2'-amino-5'-chloro-3'-fluoro[1,1'-biphenyl]-4-yl)acetate The title compound (1.15 g, 3.74 mmol, 83.9%) was obtained as an oil in the same way as in Example (1-a) using 2-bromo-4-chloro-6-fluoroaniline (1.00 g, 4.46 mmol, 1.0 g) and ethyl 2-[4-(4,4,5,5-tetramethyl-1,3,2-dioxaborolan-2-yl)phenyl]acetate (1.56 g, 5.35 mmol).

$^1$H-NMR (CDCl$_3$) δ: 1.29 (3H, t, J=7.3 Hz), 3.66 (2H, s), 4.19 (2H, q, J=7.2 Hz), 6.92 (1H, dd, J=2.4, 1.5 Hz), 7.01 (1H, dd, J=10.7, 2.4 Hz), 7.39 (4H, s).

<11-b> Ethyl {5'-chloro-3'-fluoro-2'-[(5-methylpyridine-3-sulfonyl)amino][1,1'-biphenyl]-4-yl}acetate The title compound (153 mg, 0.331 mmol, 42.4%) was obtained as an oil in the same way as in Example (1-b) using ethyl (2'-amino-5'-chloro-3'-fluoro[1,1'-biphenyl]-4-yl)acetate (240 mg, 0.780 mmol) obtained in Example (11-a) and 5-methylpyridine-3-sulfonyl chloride; hydrochloride (180 mg, 0.936 mmol).

¹H-NMR (CDCl₃) δ: 1.29 (3H, t, J=7.1 Hz), 2.33 (3H, s), 3.64 (2H, s), 4.19 (2H, q, J=7.2 Hz), 6.34 (1H, br s), 7.11-7.15 (2H, m), 7.20 (2H, dt, J=8.3, 1.7 Hz), 7.28 (2H, d, J=7.8 Hz), 7.66 (1H, s), 8.54 (1H, s), 8.61 (1H, d, J=1.5 Hz).
LCMS (ES): m/z 463 [M+H]⁺.

<11-c> {5'-Chloro-3'-fluoro-2'-[(5-methylpyridine-3-sulfonyl)amino][1,1'-biphenyl]-4-yl}acetic acid The title compound (118 mg, 0.271 mmol, 87.2%) was obtained as a solid in the same way as in Example (1-c) using ethyl {5'-chloro-3'-fluoro-2'-[(5-methylpyridine-3-sulfonyl)amino][1,1'-biphenyl]-4-yl}acetate (144 mg, 0.311 mmol) obtained in Example (11-b).

Example 12

{5'-Chloro-2'-[(4,5-dimethylpyridine-3-sulfonyl)amino]-3'-fluoro[1,1'-biphenyl]-4-yl}acetic acid <12-a> Ethyl {5'-chloro-2'-[(4,5-dimethylpyridine-3-sulfonyl)amino]-3'-fluoro[1,1'-biphenyl]-4-yl}acetate The title compound (170 mg, 0.356 mmol, 68.6%) was obtained as a solid in the same way as in Example (1-b) using ethyl (2'-amino-5'-chloro-3'-fluoro[1,1'-biphenyl]-4-yl)acetate (160 mg, 33.3 mmol) obtained in Example (11-a).
¹H-NMR (CDCl₃) δ: 1.29 (3H, t, J=7.3 Hz), 2.23 (3H, s), 2.35 (3H, s), 3.62 (2H, s), 4.19 (2H, q, J=7.2 Hz), 6.31 (1H, br s), 7.05 (1H, t, J=1.7 Hz), 7.11-7.15 (3H, m), 7.23 (2H, d, J=8.3 Hz), 8.42 (1H, s), 8.66 (1H, s). LCMS (ES): m/z 477 [M+H]⁺.

<12-b> {5'-Chloro-2'-[(4,5-dimethylpyridine-3-sulfonyl)amino]-3'-fluoro[1,1'-biphenyl]-4-yl}acetic acid The title compound (120 mg, 0.267 mmol, 75.0%) was obtained as a solid in the same way as in Example (1-c) using ethyl {5'-chloro-2'-[(4,5-dimethylpyridine-3-sulfonyl)amino]-3'-fluoro[1,1'-biphenyl]-4-yl}acetate (170 mg, 0.356 mmol) obtained in Example (12-a).

The following compounds were produced according to the manufacture methods described above.

Example 13

2-({3',5'-Dichloro-2'-[(pyridine-3-sulfonyl)amino][1,1'-biphenyl]-4-yl}oxy)propanoic acid Example 14

2-({3',5'-Dichloro-2'-[(pyridine-3-sulfonyl)amino][1,1'-biphenyl]-4-yl}oxy)-2-methylpropanoic acid Example 15

({3',5'-Dichloro-2'-[(5-methylpyridine-3-sulfonyl)amino][1,1'-biphenyl]-4-yl}oxy)acetic acid Example 16

({5'-Chloro-3'-fluoro-2'-[(pyridine-3-sulfonyl)amino][1,1'-biphenyl]-4-yl}oxy)acetic acid Example 17

({5'-Chloro-3'-fluoro-2'-[(5-methylpyridine-3-sulfonyl)amino][1,1'-biphenyl]-4-yl}oxy)acetic acid Example 18

2-({5'-Chloro-3'-fluoro-2'-[(5-methoxypyridine-3-sulfonyl)amino][1,1'-biphenyl]-4-yl}oxy)-2-methylpropanoic acid Example 19

2-({3',5'-Dichloro-2'-[(5-methoxypyridine-3-sulfonyl)amino][1,1'-biphenyl]-4-yl}oxy)propanoic acid Example 20

{3',5'-Dichloro-2'-[(5-methoxypyridine-3-sulfonyl)amino][1,1'-biphenyl]-4-yl}(difluoro)acetic acid Example 21

N-[3,5-Dichloro-3'-fluoro-4'-(methanesulfonyl)[1,1'-biphenyl]-2-yl]-5-methoxypyridine-3-sulfonamide Example 22

{3',5'-Dichloro-2'-[(5-methoxypyridine-3-sulfonyl)amino][1,1'-biphenyl]-4-yl}acetic acid Example 23

2-({5'-Chloro-3'-fluoro-2'-[(4-methylpyrimidine-5-sulfonyl)amino][1,1'-biphenyl]-4-yl}oxy)-2-methylpropanoic acid Example 24

2-({5'-Chloro-2'-[(4-ethylpyridine-3-sulfonyl)amino]-3'-fluoro[1,1'-biphenyl]-4-yl}oxy)-2-methylpropanoic acid Example 25

2-({5'-Chloro-3'-fluoro-2'-[(4-methoxypyridine-3-sulfonyl)amino][1,1'-biphenyl]-4-yl}oxy)-2-methylpropanoic acid Example 26

2-{[5'-Chloro-3'-fluoro-2'-({5-[(propan-2-yl)oxy]pyridine-3-sulfonyl}amino)[1,1'-biphenyl]-4-yl]oxy}-2-methylpropanoic acid Example 27

2-({5'-Chloro-3,3'-difluoro-2'-[(5-methylpyridine-3-sulfonyl)amino][1,1'-biphenyl]-4-yl}oxy)-2-methylpropanoic acid

Example 28

2-[(5'-Chloro-3'-fluoro-2'-{[5-(methanesulfonyl)pyridine-3-sulfonyl]amino}[1,1'-biphenyl]-4-yl)oxy]-2-methylpropanoic acid

Example 29

3-{5'-Chloro-2'-[(5-ethylpyridine-3-sulfonyl)amino]-3'-fluoro[1,1'-biphenyl]-4-yl}propanoic acid

Example 30

3-[5'-Chloro-3'-fluoro-2'-({5-[(propan-2-yl)oxy]pyridine-3-sulfonyl}amino)[1,1'-biphenyl]-4-yl]propanoic acid

Example 31

3-{5'-Chloro-2'-[(4,5-dimethylpyridine-3-sulfonyl)amino]-3'-fluoro[1,1'-biphenyl]-4-yl}propanoic acid

Example 32

2-{5'-Chloro-3'-fluoro-2'-[(5-methylpyridine-3-sulfonyl)amino][1,1'-biphenyl]-4-yl}propanoic acid

Example 33

2-{5'-Chloro-3'-fluoro-2'-[(5-methylpyridine-3-sulfonyl)amino][1,1'-biphenyl]-4-yl}butanoic acid Hereinafter, physicochemical data on the compounds described in Examples 1 to 33 and the chemical structures of corresponding compounds in a free form will be shown.

The compounds shown as salts in Examples were produced as the salts.

TABLE 1

| Ex. No. | Compound structure | Physical data |
| --- | --- | --- |
| 1 | 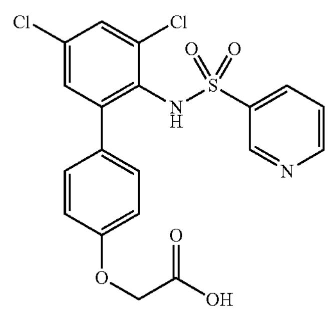 | $^1$H-NMR (DMSO-$d_6$) δ: 4.66 (2H, s), 6.67 (2H, d, J = 8.5 Hz), 7.15 (2H, d, J = 8.5 Hz), 7.30-7.34 (2H, m), 7.56-7.58 (1H, m), 7.71 (1H, d, J = 2.4 Hz), 8.47 (1H, d, J = 2.4 Hz), 8.58-8.63 (1H, m), 10.23 (1H, br s), 13.10 (1H, br s). LCMS (ES): m/z 453.1 [M + H]$^+$. |
| 2 | 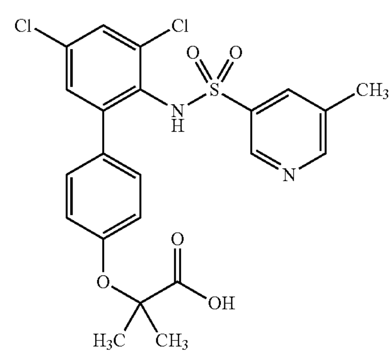 [SMILES: Cc1cncc(S(=O)(=O)Nc2c(Cl)cc(Cl)cc2-c2ccc(OC(C)(C)C(=O)O)cc2)c1] | $^1$H-NMR (DMSO-$d_6$) δ: 1.52 (6H, s), 2.24 (3H, s), 6.54-6.62 (2H, m), 7.11-7.18 (2H, m), 7.31 (1H, d, J = 2.4 Hz), 7.36-7.41 (1H, m), 7.72 (1H, d, J = 2.4 Hz), 8.31 (1H, d, J = 2.4 Hz), 8.42 (1H, d, J = 1.2 Hz), 10.16 (1H, br s), 13.13 (1H, br s). LCMS (ES): m/z 495 [M + H]$^+$. |
| 3 | 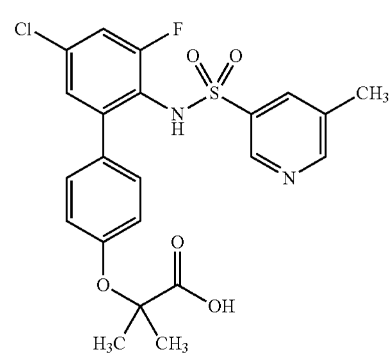 [SMILES: Cc1cncc(S(=O)(=O)Nc2c(F)cc(Cl)cc2-c2ccc(OC(C)(C)C(=O)O)cc2)c1] | $^1$H-NMR (CDCl$_3$) δ: 1.70 (6H, s), 2.41 (3H, s), 6.61-6.82 (3H, br m), 6.97-7.02 (2H, m), 7.06-7.09 (1H, m), 7.19 (1H, dd, J = 8.5, 2.4 Hz), 7.24-7.28 (1H, m), 7.74-7.76 (1H, br m), 8.10-8.12 (1H, br m), 8.52-8.55 (1H, br m). LCMS (ES): m/z 479 [M + H]$^+$. |

TABLE 1-continued

| Ex. No. | Compound structure | Physical data |
|---|---|---|
| 4 | 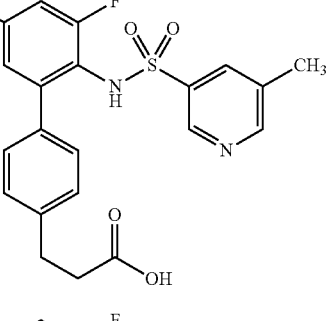 | ¹H-NMR (CD₃OD) δ: 2.30 (3H, s), 2.60 (2H, t, J = 7.8 Hz), 2.89 (2H, t, J = 7.8 Hz), 7.08-7.15 (5H, m), 7.29 (1H, dd, J = 9.3, 2.4 Hz), 7.58 (1H, s), 8.35 (1H, d, J = 2.0 Hz), 8.43 (1H, d, J = 1.5 Hz). LCMS (ES): m/z 449 [M + H]⁺. |
| 5 | 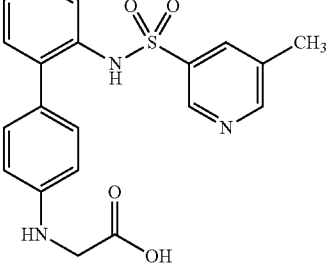 | ¹H-NMR (CD₃OD) δ: 2.31 (3H, s), 3.85 (2H, s), 6.41 (2H, d, J = 8.8 Hz), 6.95 (2H, d, J = 8.8 Hz), 7.09 (1H, t, J = 2.0 Hz), 7.23 (1H, dd, J = 9.3, 2.4 Hz), 7.51 (1H, s), 8.44-8.36 (2H, m). LCMS (ES): m/z 450 [M + H]⁺. |
| 6 | 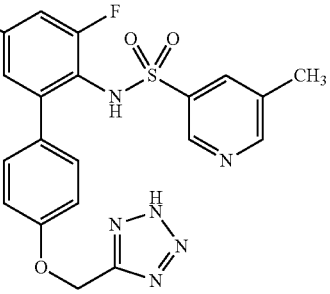 | ¹H-NMR (CD₃OD) δ: 2.28 (3H, s), 5.47 (2H, s), 6.92 (2H, dt, J = 9.4, 2.4 Hz), 7.14-7.18 (3H, m), 7.29 (1H, dd, J = 9.2, 2.5 Hz), 7.58 (1H, s), 8.33 (1H, d, J = 2.0 Hz), 8.42 (1H, d, J = 1.6 Hz). LCMS (ES): m/z 475 [M + H]⁺. |
| 7 | 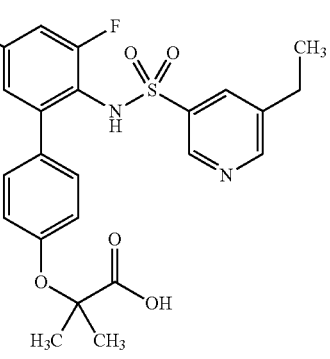 | ¹H-NMR (CD₃OD) δ: 1.25 (3H, t, J = 7.6 Hz), 1.59 (6H, s), 2.71 (2H, q, J = 7.6 Hz), 6.77 (2H, d, J = 8.8 Hz), 7.14 (2H, d, J = 8.8 Hz), 7.14-7.17 (1H, m), 7.25 (1H, dd, J = 9.3, 2.4 Hz), 7.68 (1H, t, J = 2.0 Hz), 8.42 (1H, d, J = 2.4 Hz), 8.50 (1H, d, J = 2.0 Hz). LCMS (ES): m/z 493 [M + H]⁺. |
| 8 | 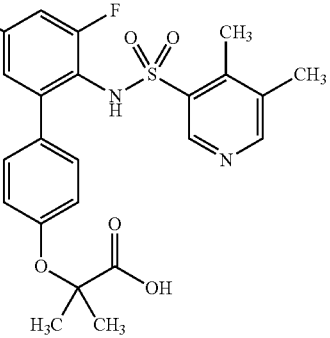 | ¹H-NMR (DMSO-d₆) δ: 1.54 (6H, s), 2.17 (3H, s), 2.25 (3H, s), 6.60 (2H, d, J = 8.3 Hz), 7.02 (2H, d, J = 8.8 Hz), 7.12 (1H, s), 7.55 (1H, d, J = 7.8 Hz), 8.26 (1H, s), 8.34 (1H, s), 10.09 (1H, s). LCMS (ES): m/z 493 [M + H]⁺. |

TABLE 1-continued

| Ex. No. | Compound structure | Physical data |
|---|---|---|
| 9 | 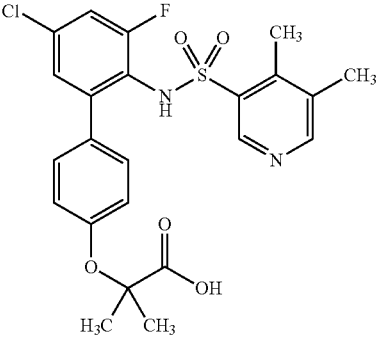 [SMILES: Cc1cncc(S(=O)(=O)Nc2c(F)cc(Cl)cc2-c2ccc(OC(C)(C)C(=O)O)cc2)c1C]<br>'potassium salt' | ¹H-NMR (DMSO-d₆) δ: 1.48 (6H, s), 2.13 (3H, s), 2.28 (3H, s), 6.60 (2H, d, J = 8.3 Hz), 6.86 (1H, s), 7.07 (1H, s), 7.17 (2H, d, J = 7.8 Hz), 8.16 (1H, s), 8.39 (1H, s).<br>LCMS (ES): m/z 493 [M + H − K]⁺. |
| 10 | 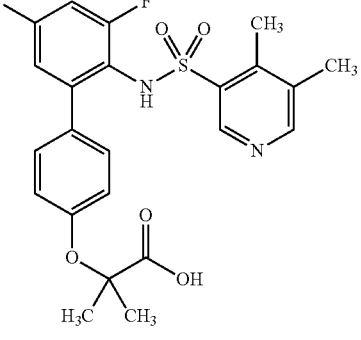<br>'sodium salt' | ¹H-NMR (DMSO-d₆) δ: 1.48 (6H, s), 2.14 (3H, s), 2.28 (3H, s), 6.61 (2H, d, J = 8.8 Hz), 6.87 (1H, s), 7.08 (1H, s), 7.17 (2H, d, J = 7.8 Hz), 8.17 (1H, s), 8.39 (1H, s).<br>LCMS (ES): m/z 493 [M + H − Na]⁺. |
| 11 | 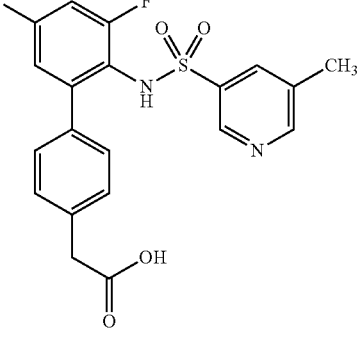 | ¹H-NMR (DMSO-d₆) δ: 2.23 (3H, s), 3.55 (2H, s), 7.15 (2H, d, J = 7.8 Hz), 7.23 (2H, d, J = 8.3 Hz), 7.24 (1H, br s), 7.47 (1H, s), 7.54 (1H, d, J = 7.3 Hz), 8.38 (1H, s), 8.48 (1H, s), 10.08 (1H, br s), 12.37 (1H, br s).<br>LCMS (ES): m/z 435 [M + H]⁺. |
| 12 | 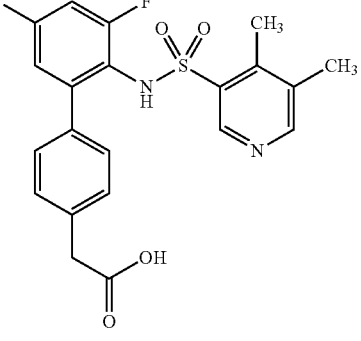 | ¹H-NMR (DMSO-d₆) δ: 2.10 (3H, s), 2.22 (3H, s), 3.53 (2H, s), 7.02 (2H, d, J = 7.8 Hz), 7.07 (2H, d, J = 7.8 Hz), 7.14 (1H, s), 7.57 (1H, dd, J = 9.3, 2.0 Hz), 8.23 (1H, s), 8.32 (1H, s), 10.09 (1H, s), 12.36 (1H, s).<br>LCMS (ES): m/z 449 [M + H]⁺. |

TABLE 1-continued

| Ex. No. | Compound structure | Physical data |
|---|---|---|
| 13 | 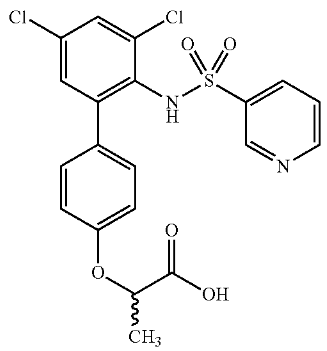 [SMILES: CC(Oc1ccc(-c2cc(Cl)cc(Cl)c2NS(=O)(=O)c2cccnc2)cc1)C(=O)O] | ¹H-NMR (DMSO-d₆) δ: 1.55 (3H, d, J = 6.7 Hz), 4.77 (1H, q, J = 6.7 Hz), 6.58-6.64 (2H, m), 7.11-7.16 (2H, m), 7.27-7.35 (2H, m), 7.53-7.60 (1H, m), 7.72 (1H, d, J = 2.4 Hz), 8.48 (1H, d, J = 2.4 Hz), 8.61 (1H, dd, J = 4.9, 1.8 Hz), 10.22 (1H, br s), 13.13 (1H, br s).<br>LCMS (ES): m/z 467 [M + H]⁺. |
| 14 | 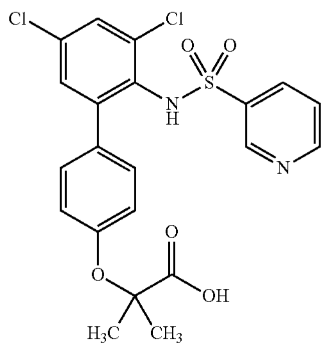 [SMILES: CC(C)(Oc1ccc(-c2cc(Cl)cc(Cl)c2NS(=O)(=O)c2cccnc2)cc1)C(=O)O] | ¹H-NMR (DMSO-d₆) δ: 1.55 (6H, s), 6.54-6.60 (2H, m), 7.10-7.16 (2H, m), 7.26-7.35 (2H, m), 7.60 (1H, dt, J = 8.1, 2.0 Hz), 7.72 (1H, d, J = 2.4 Hz), 8.49 (1H, d, J = 2.4 Hz), 8.62 (1H, dd, J = 4.9, 1.2 Hz), 10.22 (1H, s), 13.17 (1H, br s).<br>LCMS (ES): m/z 481 [M + H]⁺. |
| 15 | 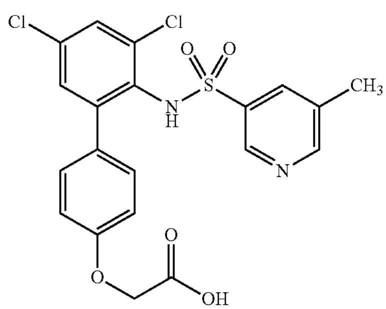 | ¹H-NMR (DMSO-d₆) δ: 2.21 (3H, s), 4.63 (2H, s), 6.63-6.71 (2H, m), 7.09-7.17 (2H, m), 7.29-7.34 (2H, m), 7.73 (1H, d, J = 2.4 Hz), 8.31 (1H, d, J = 1.8 Hz), 8.43 (1H, d, J = 1.8 Hz), 10.18 (1H, s), 13.08 (1H, br s).<br>LCMS (ES): m/z 467 [M + H]⁺. |
| 16 | 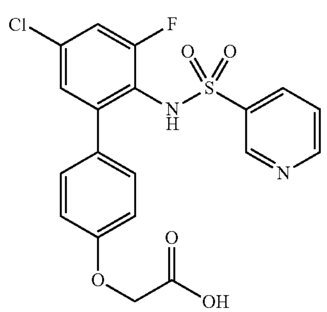 [SMILES: O=C(O)COc1ccc(-c2cc(Cl)cc(F)c2NS(=O)(=O)c2cccnc2)cc1] | ¹H-NMR (DMSO-d₆) δ: 4.70 (2H, s), 6.78 (2H, d, J = 8.5 Hz), 7.18-7.24 (3H, m), 7.37 (1H, dd, J = 8.5, 4.9 Hz), 7.51 (1H, dd, J = 9.7, 2.4 Hz), 7.68 (1H, dt, J = 7.9, 1.8 Hz), 8.55 (1H, d, J = 1.8 Hz), 8.66 (1H, d, J = 4.9 Hz), 10.14 (1H, br s), 13.09 (1H, br s).<br>LCMS (ES): m/z 437 [M + H]⁺. |
| 17 | 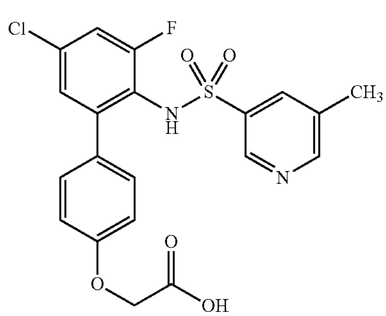 | ¹H-NMR (DMSO-d₆) δ: 2.23 (3H, s), 4.67 (2H, s), 6.77 (2H, d, J = 9.1 Hz), 7.13-7.24 (3H, m), 7.41-7.44 (1H, m), 7.53 (1H, dd, J = 9.1, 2.4 Hz), 8.35 (1H, d, J = 1.8 Hz), 8.48 (1H, d, J = 1.2 Hz), 10.10 (1H, br s), 13.09 (1H, br s).<br>LCMS (ES): m/z 451 [M + H]⁺. |

TABLE 1-continued

| Ex. No. | Compound structure | Physical data |
| --- | --- | --- |
| 18 | 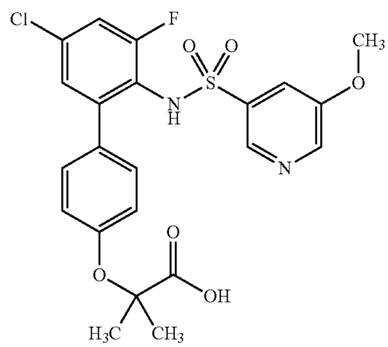 [SMILES: COc1cncc(S(=O)(=O)Nc2c(F)cc(Cl)cc2-c2ccc(OC(C)(C)C(=O)O)cc2)c1] | $^1$H-NMR (CDCl$_3$) δ: 1.70 (6H, s), 3.88 (3H, s), 6.53-6.65 (1H, br m), 6.74-6.81 (2H, m), 6.96-7.03 (2H, m), 7.07-7.09 (1H, m), 7.19 (1H, dd, J = 9.1, 2.4 Hz), 7.26 (1H, d, J = 1.8 Hz), 7.35-7.37 (1H, m), 7.94 (1H, br s), 8.38 (1H, d, J = 3.0 Hz).<br>LCMS (ES): m/z 495 [M + H]$^+$. |
| 19 | 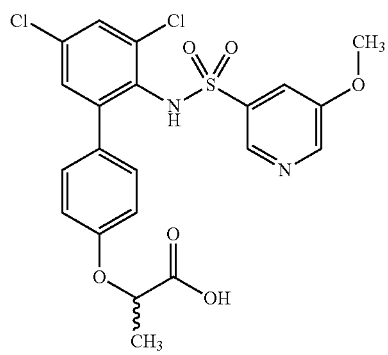 [SMILES: COc1cncc(S(=O)(=O)Nc2c(Cl)cc(Cl)cc2-c2ccc(OC(C)C(=O)O)cc2)c1] | $^1$H-NMR (DMSO-d$_6$) δ: 1.55 (3H, d, J = 6.7 Hz), 3.78 (3H, s), 4.71 (1H, q, J = 6.9 Hz), 6.55-6.61 (2H, m), 6.96-6.99 (1H, m), 7.08-7.14 (2H, m), 7.33 (1H, d, J = 2.4 Hz), 7.73 (1H, d, J = 2.4 Hz), 8.10 (1H, d, J = 1.8 Hz), 8.32 (1H, d, J = 3.1 Hz), 10.23 (1H, br s), 13.07 (1H, br s).<br>LCMS (ES): m/z 497 [M + H]$^+$. |
| 20 | 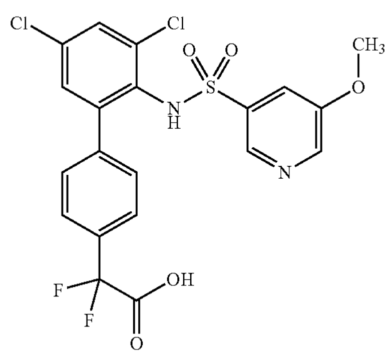 [SMILES: COc1cncc(S(=O)(=O)Nc2c(Cl)cc(Cl)cc2-c2ccc(C(F)(F)C(=O)O)cc2)c1] | $^1$H-NMR (CD$_3$OD) δ: 3.35 (9H, s), 3.82 (3H, s), 7.18 (1H, s), 7.27 (3H, t, J = 5.4 Hz), 7.46 (2H, d, J = 8.3 Hz), 7.59 (1H, d, J = 2.4 Hz), 8.13 (1H, s), 8.25 (1H, d, J = 2.4 Hz).<br>LCMS (ES): m/z 503 [M + H]$^+$. |
| 21 | 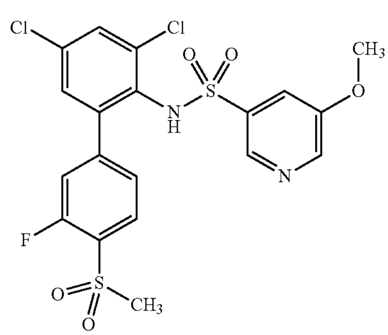 | $^1$H-NMR (CD$_3$OD) δ: 3.31 (3H, s), 3.87 (3H, s), 7.28 (1H, t, J = 2.0 Hz), 7.31-7.35 (3H, m), 7.39 (1H, dd, J = 9.3, 2.4 Hz), 7.82 (1H, t, J = 7.8 Hz), 8.16 (1H, d, J = 2.0 Hz), 8.33 (1H, d, J = 2.9 Hz).<br>LCMS (ES): m/z 489 [M + H]$^+$. |

TABLE 1-continued

| Ex. No. | Compound structure | Physical data |
| --- | --- | --- |
| 22 | 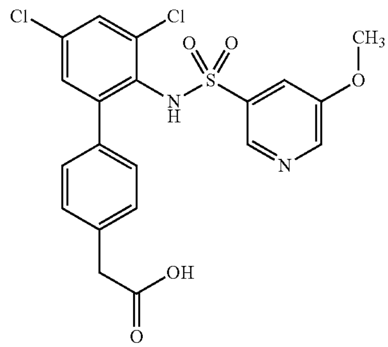 [SMILES: COc1cncc(S(=O)(=O)Nc2c(Cl)cc(Cl)cc2-c2ccc(CC(=O)O)cc2)c1] | ¹H-NMR (CD₃OD) δ: 3.50 (2H, s), 3.83 (3H, s), 7.07-7.12 (5H, m), 7.27 (1H, d, J = 2.4 Hz), 7.59 (1H, d, J = 2.4 Hz), 8.11 (1H, d, J = 2.0 Hz), 8.27 (1H, d, J = 2.9 Hz). LCMS (ES): m/z 467 [M + H]⁺. |
| 23 | 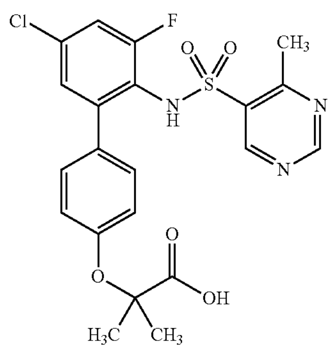 [SMILES: Cc1ncncc1S(=O)(=O)Nc1c(F)cc(Cl)cc1-c1ccc(OC(C)(C)C(=O)O)cc1] | ¹H-NMR (CD₃OD) δ: 1.62 (6H, s), 2.61 (3H, s), 6.70 (2H, dd, J = 6.8, 2.0 Hz), 7.02 (2H, dd, J = 6.8, 2.0 Hz), 7.09 (1H, t, J = 2.0 Hz), 7.29 (1H, dd, J = 9.0, 2.2 Hz), 8.56 (1H, s), 8.98 (1H, s). LCMS (ES): m/z 480 [M + H]⁺. |
| 24 | 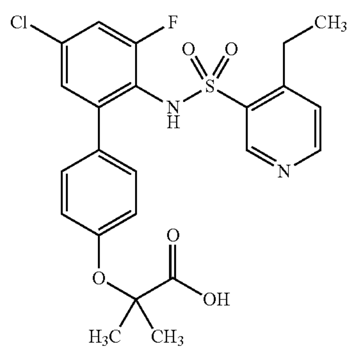 [SMILES: CCc1ccncc1S(=O)(=O)Nc1c(F)cc(Cl)cc1-c1ccc(OC(C)(C)C(=O)O)cc1] | ¹H-NMR (CD₃OD) δ: 1.20 (3H, t, J = 7.6 Hz), 1.60 (6H, s), 2.81 (2H, q, J = 7.5 Hz), 6.66 (2H, d, J = 8.8 Hz), 6.93 (2H, d, J = 8.8 Hz), 7.05 (1H, t, J = 2.0 Hz), 7.22 (1H, d, J = 5.4 Hz), 7.27 (1H, dd, J = 8.8, 2.4 Hz), 8.43 (1H, s), 8.45 (1H, d, J = 4.9 Hz). LCMS (ES): m/z 493 [M + H]⁺. |
| 25 | 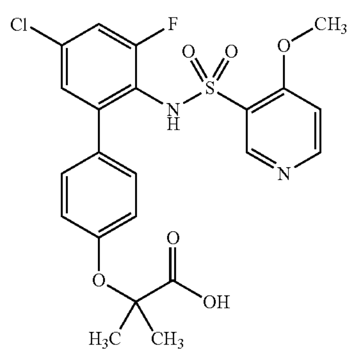 [SMILES: COc1ccncc1S(=O)(=O)Nc1c(F)cc(Cl)cc1-c1ccc(OC(C)(C)C(=O)O)cc1] | ¹H-NMR (CD₃OD) δ: 1.60 (6H, s), 3.93 (3H, s), 6.69 (2H, d, J = 6.8 Hz), 6.99-7.02 (3H, m), 7.05 (1H, t, J = 2.0 Hz), 7.26 (1H, dd, J = 9.3, 2.4 Hz), 8.30 (1H, s), 8.43 (1H, d, J = 5.9 Hz). LCMS (ES): m/z 495 [M + H]⁺. |

TABLE 1-continued

| Ex. No. | Compound structure | Physical data |
|---|---|---|
| 26 | 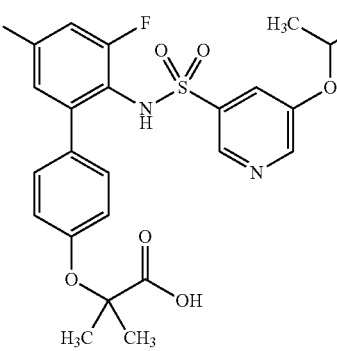 | ¹H-NMR (CD₃OD) δ: 1.36 (6H, d, J = 5.9 Hz), 1.60 (6H, s), 4.61-4.65 (1H, m), 6.79 (2H, dd, J = 6.6, 2.2 Hz), 7.17-7.13 (3H, m), 7.25 (1H, dd, J = 9.3, 2.4 Hz), 7.30 (1H, t, J = 2.2 Hz), 8.14 (1H, d, J = 1.5 Hz), 8.26 (1H, d, J = 2.9 Hz). LCMS (ES): m/z 523 [M + H]⁺. |
| 27 | 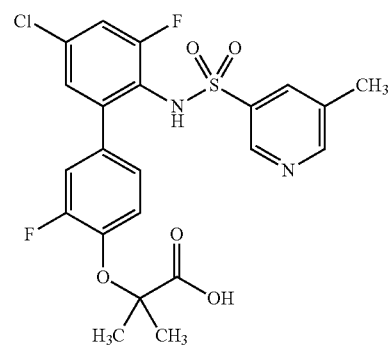 [SMILES: Cc1cncc(S(=O)(=O)Nc2c(F)cc(Cl)cc2-c2ccc(OC(C)(C)C(=O)O)c(F)c2)c1] | ¹H-NMR (CD₃OD) δ: 1.58 (6H, s), 2.35 (3H, s), 6.90-6.96 (2H, m), 7.02-6.99 (1H, m), 7.18 (1H, t, J = 2.0 Hz), 7.30 (1H, dd, J = 9.3, 2.4 Hz), 7.63 (1H, s), 8.40 (1H, d, J = 2.0 Hz), 8.48 (1H, d, J = 1.5 Hz). LCMS (ES): m/z 497 [M + H]⁺. |
| 28 | 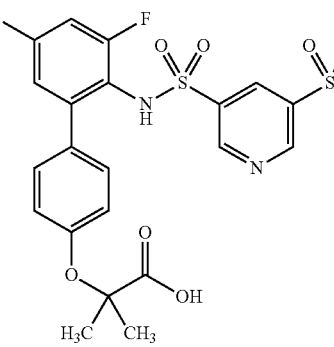 | ¹H-NMR (CD₃OD) δ: 1.59 (6H, s), 3.27 (3H, s), 6.73 (2H, dd, J = 6.8, 2.0 Hz), 7.14 (2H, dd, J = 6.8, 2.0 Hz), 7.16 (1H, t, J = 2.0 Hz), 7.29 (1H, dd, J = 9.0, 2.2 Hz), 8.32 (1H, t, J = 2.0 Hz), 8.83 (1H, d, J = 2.4 Hz), 9.15 (1H, d, J = 2.4 Hz). LCMS (ES): m/z 543 [M + H]⁺. |
| 29 | 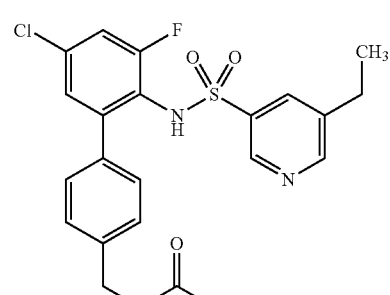 | ¹H-NMR (CD₃OD) δ: 1.23 (3H, t, J = 10.3 Hz), 2.61 (2H, t, J = 7.6 Hz), 2.66 (2H, q, J = 7.6 Hz), 2.90 (2H, t, J = 7.8 Hz), 7.11 (2H, d, J = 8.3 Hz), 7.16-7.13 (3H, m), 7.28 (1H, dd, J = 9.0, 2.2 Hz), 7.65 (1H, t, J = 2.0 Hz), 8.36 (1H, d, J = 2.0 Hz), 8.47 (1H, d, J = 2.0 Hz). LCMS (ES): m/z 463 [M + H]⁺. |

TABLE 1-continued

| Ex. No. | Compound structure | Physical data |
|---|---|---|
| 30 | 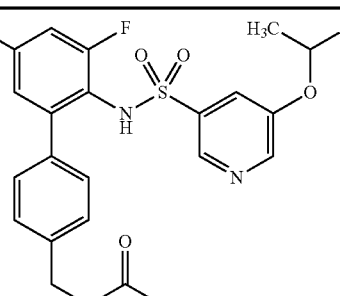 | $^1$H-NMR (CD$_3$OD) δ: 1.34 (6H, d, J = 6.3 Hz), 2.62 (2H, t, J = 7.8 Hz), 2.90 (2H, t, J = 7.8 Hz), 4.57-4.62 (1H, m), 7.10 (2H, d, J = 8.3 Hz), 7.14 (2H, d, J = 8.3 Hz), 7.16 (1H, s), 7.24 (1H, t, J = 2.2 Hz), 7.28 (1H, dd, J = 8.8, 2.4 Hz), 8.09 (1H, d, J = 2.0 Hz), 8.24 (1H, d, J = 2.9 Hz). LCMS (ES): m/z 493 [M + H]$^+$. |
| 31 | 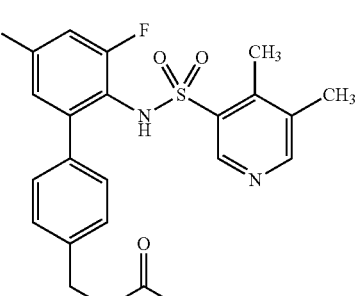 | $^1$H-NMR (CD$_3$OD) δ: 2.20 (3H, s), 2.33 (3H, s), 2.58 (2H, t, J = 7.6 Hz), 2.88 (2H, t, J = 7.8 Hz), 6.97 (2H, d, J = 7.8 Hz), 7.02 (2H, d, J = 7.8 Hz), 7.05 (1H, t, J = 2.0 Hz), 7.31 (1H, dd, J = 9.0, 2.2 Hz), 8.29 (2H, br s). LCMS (ES): m/z 463 [M + H]$^+$. |
| 32 | 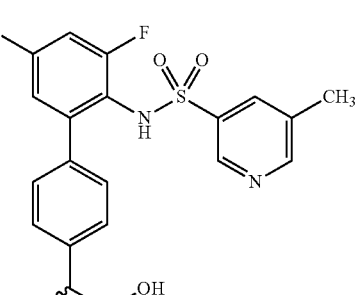 | $^1$H-NMR (DMSO-d$_6$) δ: 1.39 (3H, d, J = 7.3 Hz), 2.26 (3H, s), 3.67 (1H, q, J = 7.0 Hz), 7.20 (2H, d, J = 8.3 Hz), 7.26-7.28 (1H, m), 7.29 (2H, d, J = 8.3 Hz), 7.56 (1H, dd, J = 9.0, 2.2 Hz), 7.56-7.58 (1H, m), 8.40 (1H, d, J = 2.0 Hz), 8.48 (1H, d, J = 1.5 Hz), 10.09 (1H, s), 12.37 (1H, s). LCMS (ES): m/z 449 [M + H]$^+$. |
| 33 | 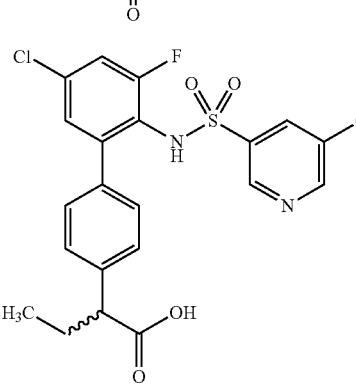 | $^1$H-NMR (DMSO-d$_6$) δ: 0.87 (3H, t, J = 7.3 Hz), 1.60-1.67 (1H, m), 1.90-1.99 (1H, m), 2.26 (3H, s), 3.40 (1H, t, J = 8.8 Hz), 7.21 (2H, d, J = 8.3 Hz), 7.27-7.25 (1H, m), 7.29 (2H, d, J = 4.1 Hz), 7.54 (1H, dd, J = 9.3, 2.4 Hz), 7.57-7.59 (1H, m), 8.41 (1H, d, J = 2.0 Hz), 8.47 (1H, d, J = 1.5 Hz), 10.06 (1H, s), 12.38 (1H, s). LCMS (ES): m/z 463 [M + H]$^+$. |

<Test Examples>
(Test Example 1) Inhibitory Test of TNAP Activity

COS1 cells (DS Pharma Biomedical Co., Ltd.) were transfected with human TNAP (OriGene Technologies, Inc.) using Lipofectamine LTX & Plus reagent (Invitrogen Corp.). On the next day, the medium was replaced with a fresh medium, and the cells were cultured in an incubator for 3 days. After 3 days, the culture supernatant was collected and concentrated by centrifugation at 5000 G for 30 minutes using Amicon 14, 10$^4$ cut (Merck Millipore). The concentrated culture supernatant was dialyzed against 5 L of 50 mM Tris/200 mM NaCl/1 mM MgCl$_2$/20 μM ZnCl$_2$ twice and used as an enzyme source (enzyme solution). The substrate pNPP (ProteoChem Inc.) was adjusted to 3.1 mM with Milli-Q water, and a solution of each test compound dissolved in dimethyl sulfoxide (DMSO; Wako Pure Chemical Industries, Ltd.) by 6 serial dilutions at a 5-fold common ratio from 100 μM or DMSO was added thereto at a final concentration of 1% by volume. The enzyme solution adjusted to 2 μg/mL with an assay buffer (200 mM Tris/2 mM MgCl$_2$/0.04 mM ZnCl$_2$/0.01% Tween 20) was added in the same amount of the substrate solution and incubated at room temperature for 60 minutes. Then, the absorbance (ABS: 405 nm) was measured using a microplate reader (model plus 384, Molecular Devices, LLC), and the concentration of produced p-nitrophenol was calculated. The inhibition of human TNAP activity by the test compound was evaluated on the basis of the concentration $IC_{50}$ at which each test compound suppressed 50% of p-nitrophenol production.

The results are shown in Table 2.

TABLE 2

| Example compound No. | IC50 (nM) |
|---|---|
| 1 | 5.5 |
| 2 | 0.50 |
| 3 | 0.24 |
| 4 | 0.27 |
| 5 | 0.39 |
| 6 | 0.26 |
| 7 | 0.15 |
| 8 | 0.15 |
| 11 | 0.14 |
| 12 | 0.10 |
| 13 | 3.5 |
| 14 | 2.6 |
| 15 | 0.90 |
| 16 | 2.4 |
| 17 | 0.30 |
| 18 | 0.23 |
| 19 | 0.49 |
| 20 | 0.36 |
| 21 | 1.2 |
| 22 | 0.28 |
| 23 | 2.4 |
| 24 | 0.20 |
| 25 | 0.41 |
| 26 | 0.19 |
| 27 | 0.68 |
| 28 | 2.6 |
| 29 | 0.18 |
| 30 | 0.24 |
| 31 | 0.18 |
| 32 | 0.17 |
| 33 | 0.14 |

The compound of the present invention exhibits the excellent inhibition of human TNAP activity and is useful as a pharmaceutical for the treatment or prophylaxis of ectopic calcification, etc.

(Test Example 2) Specific Inhibitory Test of TNAP Activity

COS1 cells (DS Pharma Biomedical Co., Ltd.) were transfected with human IAP (small-intestinal alkaline phosphatase, purchased from OriGene Technologies, Inc.) or human PLAP (placental alkaline phosphatase, purchased from OriGene Technologies, Inc.) using Lipofectamine LTX & Plus reagent (Invitrogen Corp.). On the next day, the medium was replaced with a fresh medium, and the cells were cultured in an incubator for 3 days. After 3 days, the culture supernatant was collected and concentrated by centrifugation at 5000 G for 30 minutes using Amicon 14, $10^4$ cut (Merck Millipore). The concentrated culture supernatant was dialyzed against 5 L of 50 mM Tris/200 mM NaCl/1 mM $MgCl_2$/20 μM $ZnCl_2$ twice and used as an enzyme source (enzyme solution). The substrate pNPP (ProteoChem Inc.) was adjusted to 3.1 mM with Milli-Q water, and a solution of each test compound dissolved in dimethyl sulfoxide (DMSO; Wako Pure Chemical Industries, Ltd.) by 6 serial dilutions at a 5-fold common ratio from 100 μM or DMSO was added thereto at a final concentration of 1% by volume. The enzyme solution of human IAP or human PLAP adjusted to 2 μg/mL with an assay buffer (200 mM Tris/2 mM $MgCl_2$/0.04 mM $ZnCl_2$/0.01% Tween 20) was added in the same amount of the substrate solution and incubated at room temperature for 60 minutes. Then, the absorbance (ABS: 405 nm) was measured using a microplate reader (model plus 384, Molecular Devices, LLC), and the concentration of produced p-nitrophenol was calculated. The inhibition of human IAP or PLAP activity by the test compound was evaluated on the basis of the concentration $IC_{50}$ at which each test compound suppressed 50% of p-nitrophenol production.

The compound of the present invention exhibits the excellent specific inhibition of TNAP activity and is useful as a pharmaceutical for the treatment or prophylaxis of ectopic calcification, etc.

(Test Example 3) Inhibitory Test of Plasma TNAP Activity in B6 Mouse (Charles River Laboratories Japan, Inc.)

After blood sampling from the tail vein using a heparin-treated hematocrit capillary tube (EM Meister Hematocrit Capillary Tube, AS ONE Corp.) (as the sample before compound administration), each test compound suspended in a 0.5% methylcellulose solution (powder purchased from Wako Pure Chemical Industries, Ltd. was adjusted to 0.5% with Otsuka distilled water) was administered orally to the mouse (0.3 mg/kg). 1, 2, 4, 6, and 24 hours after the administration, blood was collected from the tail vein using a heparin-treated hematocrit capillary tube to obtain a plasma sample. The plasma sample was added to an assay buffer (1 M Tris, 1 M $MgCl_2$, 20 mM $ZnCl_2$, and water, pH 7.5), and the mixture was left standing for 5 minutes. Then, the absorbance at 405 nm was measured and used as a blank. The substrate pNPP was added to the plasma sample and incubated at room temperature for 180 minutes. Then, the absorbance (ABS: 405 nm) was measured using a microplate reader (model plus 384, Molecular Devices, LLC), and the concentration of produced p-nitrophenol was calculated. The blank was subtracted from all measurement values to calculate TNAP activity at each time point with the TNAP activity of the sample before compound administration defined as 100%.

The pharmacological effect of the test compound was evaluated by the average inhibition of plasma ALP (80-90% containing TNAP) activity for 6 hours from 0 hour to 6 hours after the administration of the test compound. It was calculated according to the following expression:

100−((plasma ALP activity at 0 hr+plasma ALP activity at 1 hr)*1/2+(plasma ALP activity at 1 hr+plasma ALP activity at 2 hr)*1/2+(plasma ALP activity at 2 hr+plasma ALP activity at 4 hr)*2/2+(plasma ALP activity at 4 hr+plasma ALP activity at 6 hr)*2/2)/6.

The results are shown in Table 3.

TABLE 3

| Example compound No. | Plasma ALP Inhibition (6 h ave. inhibition %) |
|---|---|
| 3 | 70.5 |
| 4 | 80.2 |
| 7 | 69.0 |
| 8 | 76.2 |
| 11 | 79.0 |
| 12 | 82.2 |
| 29 | 70.9 |
| 30 | 69.9 |
| 31 | 82.2 |

The compound of the present invention exhibits an excellent in vivo TNAP inhibitory effect and is useful as a pharmaceutical for the treatment or prophylaxis of ectopic calcification, etc.

(Test Example 4) In Vivo Anti-Calcification Test in Vitamin D-Induced Calcification Model A DBA/2 mouse (male, 6 weeks old when used, Charles River Laboratories Japan, Inc.) is given powder feed (FR-2 powder feed, Funabashi Farm Co., Ltd.) containing each test compound. 3.75 mg/kg cholecalciferol (Sigma-Aldrich Corp.) is intraperitoneally administered for 3 days from the next day. Seven days after the final cholecalciferol administration, the animal is sacrificed, and the thoracic aorta and the kidney are sampled. The tissue samples are freeze-dried (FREEZE DRYER, FRD-50M, Iwaki Asahi Techno Glass Corp.). Then, 10% formic acid (undiluted solution purchased from Kishida Chemical Co., Ltd. is adjusted to 10% with Milli-Q water) is added to each tissue sample, which is then homogenized using QIAGEN Retsch MM300 Tissue Lyser (Qiagen N.V.). The homogenate is centrifuged, and the supernatant is used as a sample. The calcium concentration in the sample is measured as absorbance (ABS 612 nm, Microplate reader, model plus 384, Molecular Devices, LLC) using Calcium assay kit (Wako Pure Chemical Industries, Ltd.) to calculate the amount of calcium in the tissue.

(Test Example 5) In Vivo Anti-Calcification Test in Nephrectomized Mouse

A 5/6 nephrectomized DBA/2 mouse (male, 8 weeks old) is purchased from CLEA Japan, Inc. This mouse is loaded with 1.2% high-phosphorus diet (Oriental Yeast Co., Ltd.). Each test compound suspended in a 0.5% methylcellulose solution (powder purchased from Wako Pure Chemical Industries, Ltd. is adjusted to 0.5% with Otsuka distilled water) is administered orally to the mouse. After three months, the animal is sacrificed, and the kidney is sampled. The tissue sample is freeze-dried (FREEZE DRYER, FRD-50M, Iwaki Asahi Techno Glass Corp.). Then, 10% formic acid (undiluted solution purchased from Kishida Chemical Co., Ltd. is adjusted to 10% with Milli-Q water) is added to the tissue sample, which is then homogenized using QIAGEN Retsch MM300 Tissue Lyser (Qiagen N.V.). The homogenate is centrifuged, and the supernatant is used as a sample. The calcium concentration in the sample is measured as absorbance (ABS 612 nm, Microplate reader, model plus 384, Molecular Devices, LLC) using Calcium assay kit (Wako Pure Chemical Industries, Ltd.) to calculate the amount of calcium in the tissue.

(Test Example 6) Pharmacokinetic Test

The pharmacokinetic test can be conducted according to a method well-known in the field of pharmacodynamics.

Each test compound was suspended in a 0.5% aqueous methylcellulose solution. The obtained suspension was orally administered at a dose in an appropriate range (e.g., 0.01 mg/kg to 10 mg/kg) to an animal (e.g., a mouse, a rat, a dog, or a cynomolgus monkey) generally used in the pharmacokinetic test. Also, the test compound was dissolved in saline. The obtained solution was intravenously (e.g., through the tail vein, the cephalic vein, or the saphenous vein) administered at a dose in an appropriate range (e.g., 0.1 mg/kg to 10 mg/kg) to an animal (e.g., a mouse, a rat, a dog, or a cynomolgus monkey) generally used in the pharmacokinetic test. After given times (e.g., 0.08, 0.25, 0.5, 1, 2, 4, 6, 8, and 24 hours) from the administration, blood was collected from an appropriate blood collection site (e.g., the jugular vein, the cephalic vein, or the saphenous vein). The obtained blood was centrifuged to prepare a plasma sample. The concentration of the test compound contained in the plasma sample was measured by quantitative analysis using a liquid chromatography-mass spectrometer (LC-MS/MS).

The pharmacokinetics of the test compound were evaluated on the basis of maximum plasma concentration (Cmax), area under the plasma drug concentration-time curve (AUC), total clearance (CL), and bioavailability and analyzed using software (Phoenix, etc.). Cmax represents the maximum plasma concentration of the orally administered test compound. AUC was calculated according to the trapezium rule from the plasma concentrations of the test compound from the time when the test compound was administered up to the final time when the test compound was quantifiable. The bioavailability was calculated according to the following expression:

[(AUC after oral administration/Dose of the oral administration)/(AUC after intravenous administration/Dose of the intravenous administration)].

The compound of the present invention exhibits excellent pharmacokinetics (Cmax, AUC, CL, or bioavailability) and is useful as a pharmaceutical (particularly, a pharmaceutical for the treatment or prophylaxis of ectopic calcification).

<Preparation Examples>

(Preparation Example 1) Capsule

| | |
|---|---|
| Compound of Example 31 | 50 mg |
| Lactose | 128 mg |
| Corn starch | 70 mg |
| Magnesium stearate | 2 mg |
| | 250 mg |

A powder having the formulation mentioned above is mixed and sifted through a 60-mesh sieve. Then, this powder is put in a gelatin capsule shell to prepare a capsule.

(Preparation Example 2) Tablet

| | |
|---|---|
| Compound of Example 31 | 50 mg |
| Lactose | 126 mg |
| Corn starch | 23 mg |
| Magnesium stearate | 1 mg |
| | 200 mg |

A powder having the formulation mentioned above is mixed, granulated using corn starch paste, and dried, followed by compression in a tableting machine to prepare tablets (200 mg each). This tablet can be coated, if necessary.

The novel biaryl derivative represented by the general formula (I) of the present invention or the pharmacologically acceptable salt thereof has an excellent TNAP inhibitory effect and is useful as a pharmaceutical.

What is claimed is:

1. A compound represented by formula (I):

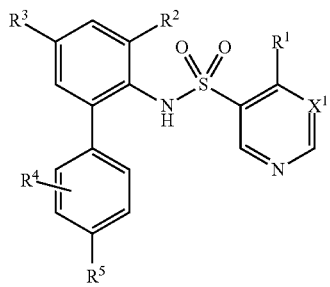

wherein $X^1$ represents a nitrogen atom or $CR^9$, $R^1$ represents a hydrogen atom, a C1-C6 alkyl group or a C1-C6 alkoxy group, $R^2$ represents a halogen atom, $R^3$ represents a hydrogen atom or a halogen atom, $R^4$ represents a hydrogen atom or a halogen atom, $R^5$ represents a C1-C3 alkylsulfonyl group, a C1-C6 alkyl group (wherein the alkyl group is substituted by one group selected from a C1-C3 alkylsulfonyl group, a carboxy group and a tetrazolyl group), a C1-C6 haloalkyl group (wherein the haloalkyl group is substituted by one group selected from a C1-C3 alkylsulfonyl group, a carboxy group and a tetrazolyl group), a C1-C6 alkoxy group (wherein the alkoxy group is substituted by one group selected from a C1-C3 alkylsulfonyl group, a carboxy group and a tetrazolyl group) or a C1-C6 alkylamino group (wherein the alkylamino group is substituted by one group selected from a C1-C3 alkylsulfonyl group, a carboxy group and a tetrazolyl group), and $R^9$ represents a hydrogen atom, a halogen atom, a C1-C3 alkylsulfonyl group, a C1-C6 alkyl group or a C1-C6 alkoxy group, or a pharmacologically acceptable salt thereof.

2. A compound according to claim 1 represented by formula (II):

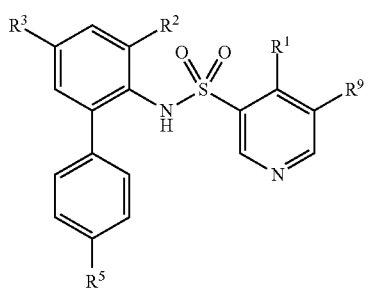

wherein $R^1$ represents a hydrogen atom or a C1-C3 alkyl group, $R^2$ represents a halogen atom, $R^3$ represents a halogen atom, $R^5$ represents a C1-C6 alkyl group (wherein the alkyl group is substituted by one group selected from a C1-C3 alkylsulfonyl group, a carboxy group and a tetrazolyl group), a C1-C6 alkoxy group (wherein the alkoxy group is substituted by one group selected from a C1-C3 alkylsulfonyl group, a carboxy group and a tetrazolyl group) or a C1-C6 alkylamino group (wherein the alkylamino group is substituted by one group selected from a C1-C3 alkylsulfonyl group, a carboxy group and a tetrazolyl group), and $R^9$ represents a C1-C3 alkyl group or a C1-C3 alkoxy group, or a pharmacologically acceptable salt thereof.

3. A compound according to claim 1 represented by formula (III):

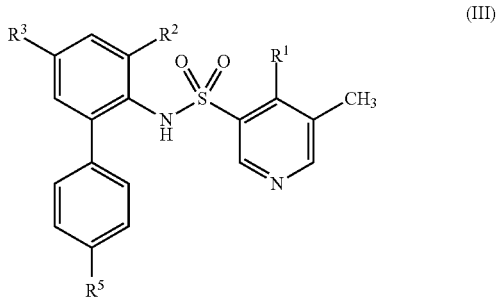

wherein $R^1$ represents a hydrogen atom, a methyl group or an ethyl group, $R^2$ represents a fluorine atom or a chlorine atom, $R^3$ represents a halogen atom, and $R^5$ represents a C1-C6 alkyl group substituted by one carboxy group or a C1-C6 alkoxy group substituted by one carboxy group, or a pharmacologically acceptable salt thereof.

4. A compound according to claim 1 represented by

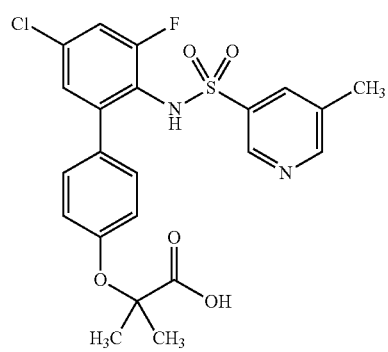 [SMILES: Cc1cncc(S(=O)(=O)Nc2c(F)cc(Cl)cc2-c2ccc(OC(C)(C)C(=O)O)cc2)c1]

or a pharmacologically acceptable salt thereof.

5. A compound according to claim 1 represented by

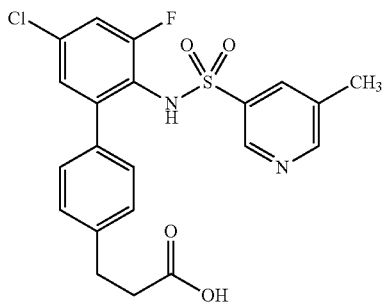

or a pharmacologically acceptable salt thereof.

6. A compound according to claim 1 represented by

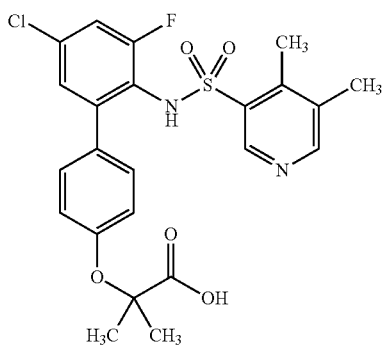 [SMILES: Cc1cncc(S(=O)(=O)Nc2c(F)cc(Cl)cc2-c2ccc(OC(C)(C)C(=O)O)cc2)c1C]

or a pharmacologically acceptable salt thereof.

7. A compound according to claim 1 represented by

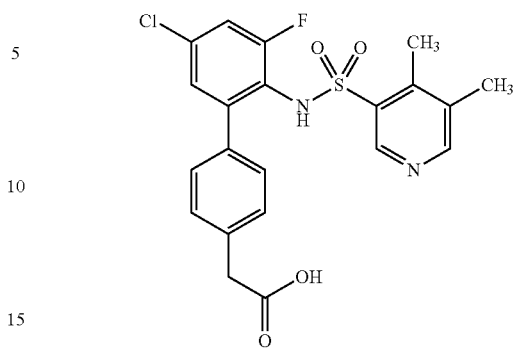

or a pharmacologically acceptable salt thereof.

8. A compound according to claim 1, wherein the pharmacologically acceptable salt is a sodium salt or a potassium salt.

9. A pharmaceutical composition comprising a compound according to claim 1, or a pharmacologically acceptable salt thereof, and a pharmaceutically acceptable carrier.

10. A method for inhibiting TNAP in a subject, comprising administering a pharmacologically effective amount of a compound according to claim 1, or a pharmacologically acceptable salt thereof to a subject in need thereof.

11. A method for the treatment of ectopic calcification, comprising administering a pharmacologically effective amount of a compound according to claim 1, or a pharmacologically acceptable salt thereof to a subject in need thereof.

12. A method for the treatment of a disease or condition selected from the group consisting of pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis, comprising administering a pharmacologically effective amount of a compound according to claim 1, or a pharmacologically acceptable salt thereof to a subject in need thereof.

13. The method according to claim 12, wherein the disease or condition is pseudoxanthoma elasticum (PXE).

14. The method according to claim 10, wherein the subject is a human.

15. The method according to claim 11, wherein the subject is a human.

16. The method according to claim 12, wherein the subject is a human.

* * * * *